(12) United States Patent
Karasic et al.

(10) Patent No.: US 12,096,929 B2
(45) Date of Patent: Sep. 24, 2024

(54) FLEXIBLE ANCHOR DELIVERY SYSTEM

(71) Applicant: Smith & Nephew, Inc., Memphis, TN (US)

(72) Inventors: Geoffrey I. Karasic, Boston, MA (US); Brett A. McKenzie, Haverhill, MA (US); Steve W. Astorino, Norfolk, MA (US); Richard M. Lunn, Kingston, MA (US); Matthew E. Koski, Westford, MA (US); Tatsuya Arai, Waltham, MA (US); Mark E. Housman, North Attleboro, MA (US); Roland F. Gatturna, Bourne, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 18/212,250

(22) Filed: Jun. 21, 2023

(65) Prior Publication Data

US 2023/0329696 A1    Oct. 19, 2023

Related U.S. Application Data

(63) Continuation of application No. 17/114,585, filed on Dec. 8, 2020, now Pat. No. 11,723,650, which is a
(Continued)

(51) Int. Cl.
*A61B 17/04* (2006.01)
*A61B 17/16* (2006.01)
*A61B 17/06* (2006.01)

(52) U.S. Cl.
CPC ...... *A61B 17/0401* (2013.01); *A61B 17/1633* (2013.01); *A61B 2017/0406* (2013.01);
(Continued)

(58) Field of Classification Search
CPC .......... A61B 17/06166; A61B 17/0401; A61B 17/0483; A61B 17/0469; A61B 17/0482;
(Continued)

(56) References Cited

U.S. PATENT DOCUMENTS 2,065,659 A    12/1936  Cullen
3,580,256 A    5/1971   Wilkinson
(Continued)

FOREIGN PATENT DOCUMENTS

CN    101888810    11/2010
EP    0328401      8/1989
(Continued)

OTHER PUBLICATIONS

"Technique for AGL reconstruction with Acufex Director Drill Guide and Endobutton CL" ©1999, Smith & Nephew, Inc., 20 pages.
(Continued)

*Primary Examiner* — Dianne Dornbusch
(74) *Attorney, Agent, or Firm* — ArentFox Schiff LLP; Joseph M. Maraia; Marlo Schepper Grolnic

(57) ABSTRACT

An assembly includes a flexible fixation member, a suture, and a delivery device. The fixation member includes a body with two terminal ends. A suture passes through the flexible fixation member at various points along a length of the body such that portions of the fixation member are slidable relative to the suture and configurable to form a cluster within a surgical site. The delivery device includes a tubular member, an elongated inserter, and a trigger. The elongated inserter is slidably disposed within the tubular member. The inserter has a forked distal end configured to receive a portion of the flexible fixation member and the suture. The trigger is finger-engagable and fixedly coupled to the proximal end of the inserter. It is configured to advance and retract
(Continued)

the inserter relative to the tubular member. The trigger includes a retention member for retaining a proximal end portion of the suture.

19 Claims, 35 Drawing Sheets

Related U.S. Application Data continuation of application No. 16/684,713, filed on Nov. 15, 2019, now Pat. No. 11,607,211, which is a continuation of application No. 16/373,090, filed on Apr. 2, 2019, now Pat. No. 10,617,408, which is a continuation of application No. 16/000,980, filed on Jun. 6, 2018, now Pat. No. 10,292,697, which is a continuation of application No. 14/433,684, filed as application No. PCT/US2013/065064 on Oct. 15, 2013, now Pat. No. 10,010,314, which is a continuation of application No. 13/654,855, filed on Oct. 18, 2012, now Pat. No. 8,986,327.

(52) U.S. Cl.
CPC . *A61B 2017/0409* (2013.01); *A61B 2017/042* (2013.01); *A61B 2017/0446* (2013.01); *A61B 2017/0454* (2013.01); *A61B 2017/0459* (2013.01); *A61B 2017/0462* (2013.01); *A61B 2017/047* (2013.01); *A61B 2017/0496* (2013.01); *A61B 17/06166* (2013.01)

(58) Field of Classification Search
CPC ...... A61B 2017/0459; A61B 2017/047; A61B 2017/0446; A61B 2017/042; A61B 2017/0496; A61B 2017/0462; A61B 2017/0454; A61B 2017/0409; A61B 2017/0406
See application file for complete search history.

(56) References Cited

U.S. PATENT DOCUMENTS

| | | | |
|---|---|---|---|
| 4,269,246 A | 5/1981 | Larson et al. | |
| 4,605,414 A | 8/1986 | Czajka | |
| 5,217,470 A | 6/1993 | Weston | |
| 5,234,445 A | 8/1993 | Walker et al. | |
| 5,306,301 A | 4/1994 | Graf et al. | |
| 5,405,352 A | 4/1995 | Weston | |
| 5,431,651 A | 7/1995 | Goble | |
| 5,449,367 A | 9/1995 | Kadry | |
| 5,451,203 A | 9/1995 | Lamb | |
| 5,484,440 A | 1/1996 | Allard | |
| 5,527,341 A | 6/1996 | Gogolewski et al. | |
| 5,578,057 A * | 11/1996 | Wenstrom, Jr. | A61B 17/0401 |
| | | | 606/232 |
| 5,645,588 A | 7/1997 | Graf et al. | |
| 5,690,649 A | 11/1997 | Li | |
| 5,718,717 A | 2/1998 | Bonutti | |
| 5,769,894 A | 6/1998 | Ferragamo | |
| 5,827,291 A * | 10/1998 | Fucci | A61B 17/0401 |
| | | | 606/232 |
| 5,893,592 A | 4/1999 | Schulze et al. | |
| 5,989,252 A | 11/1999 | Fumex | |
| 5,993,459 A | 11/1999 | Larsen et al. | |
| 6,033,405 A | 3/2000 | Winslow et al. | |
| 6,143,029 A | 11/2000 | Rippstein | |
| 6,193,754 B1 | 2/2001 | Seedhom | |
| 6,228,096 B1 * | 5/2001 | Marchand | A61B 17/0401 |
| | | | 606/232 |
| 6,296,659 B1 | 10/2001 | Foerster | |
| 6,436,100 B1 | 8/2002 | Berger | |
| 6,517,578 B2 | 2/2003 | Hein | |
| 7,390,329 B2 | 6/2008 | Westra et al. | |
| 7,390,332 B2 | 6/2008 | Selvitelli et al. | |
| 7,601,165 B2 | 10/2009 | Stone | |
| 7,658,751 B2 | 2/2010 | Stone et al. | |
| 7,731,732 B2 | 6/2010 | Ken | |
| 7,736,378 B2 | 6/2010 | Maahs et al. | |
| 7,749,250 B2 | 7/2010 | Stone et al. | |
| 7,771,455 B2 | 8/2010 | Ken | |
| 7,780,701 B1 | 8/2010 | Meridew et al. | |
| 7,905,903 B2 | 3/2011 | Stone et al. | |
| 7,905,904 B2 | 3/2011 | Stone et al. | |
| 7,909,851 B2 | 3/2011 | Stone et al. | |
| 7,959,650 B2 | 6/2011 | Kaiser et al. | |
| 7,972,292 B2 | 7/2011 | Behl et al. | |
| 8,052,696 B2 * | 11/2011 | Del Rio | A61B 17/0483 |
| | | | 606/103 |
| 8,057,511 B2 | 11/2011 | Flores et al. | |
| 8,088,130 B2 | 1/2012 | Kaiser et al. | |
| 8,118,836 B2 | 2/2012 | Denham et al. | |
| 8,128,640 B2 | 3/2012 | Harris et al. | |
| 8,128,658 B2 | 3/2012 | Kaiser et al. | |
| 8,137,382 B2 | 3/2012 | Denham et al. | |
| 8,172,871 B2 | 5/2012 | Ken | |
| 8,241,305 B2 | 8/2012 | Stone | |
| 8,298,262 B2 | 10/2012 | Stone et al. | |
| 8,303,604 B2 | 11/2012 | Stone et al. | |
| 8,308,765 B2 | 11/2012 | Saadat et al. | |
| 8,361,113 B2 | 1/2013 | Stone et al. | |
| 8,409,253 B2 | 4/2013 | Stone et al. | |
| 8,986,327 B2 | 3/2015 | Karasic et al. | |
| 9,307,977 B2 * | 4/2016 | McDevitt | A61B 17/1796 |
| 10,010,314 B2 | 7/2018 | Karasic et al. | |
| 10,292,697 B2 | 5/2019 | Karasic et al. | |
| 10,617,408 B2 | 4/2020 | Karasic et al. | |
| 11,607,211 B2 | 3/2023 | Karasic et al. | |
| 2001/0002440 A1 | 5/2001 | Bonutti | |
| 2001/0041938 A1 | 11/2001 | Hein | |
| 2002/0029066 A1 | 3/2002 | Foerster | |
| 2002/0115999 A1 | 8/2002 | McDevitt et al. | |
| 2003/0050666 A1 | 3/2003 | Grafton | |
| 2003/0130694 A1 | 7/2003 | Bojarski et al. | |
| 2003/0149448 A1 | 8/2003 | Foerster et al. | |
| 2004/0133238 A1 | 7/2004 | eerier | |
| 2004/0181234 A1 | 9/2004 | McDevitt et al. | |
| 2004/0220573 A1 | 11/2004 | McDevitt et al. | |
| 2004/0225292 A1 | 11/2004 | Sasso et al. | |
| 2005/0033364 A1 | 2/2005 | Gregoire et al. | |
| 2005/0149118 A1 | 7/2005 | Koyfman et al. | |
| 2005/0187577 A1 | 8/2005 | Selvitelli et al. | |
| 2005/0209622 A1 | 9/2005 | Carrison | |
| 2005/0251159 A1 | 11/2005 | Ewers et al. | |
| 2005/0277985 A1 | 12/2005 | Wert et al. | |
| 2006/0155328 A1 | 7/2006 | Foerster | |
| 2006/0178680 A1 | 8/2006 | Nelson et al. | |
| 2006/0229671 A1 | 10/2006 | Steiner et al. | |
| 2006/0259076 A1 | 11/2006 | Burkhart et al. | |
| 2006/0293709 A1 | 12/2006 | Bojarski et al. | |
| 2007/0010857 A1 | 1/2007 | Sugimoto et al. | |
| 2007/0016244 A1 | 1/2007 | Behl et al. | |
| 2007/0156174 A1 | 7/2007 | Kaiser et al. | |
| 2007/0185532 A1 * | 8/2007 | Stone | A61B 17/0482 |
| | | | 606/232 |
| 2007/0239209 A1 | 10/2007 | Fallman | |
| 2008/0009904 A1 * | 1/2008 | Bourque | A61B 17/0401 |
| | | | 606/232 |
| 2008/0065070 A1 | 3/2008 | Fried et al. | |
| 2008/0065114 A1 | 3/2008 | Stone et al. | |
| 2008/0140092 A1 | 6/2008 | Stone et al. | |
| 2008/0140093 A1 | 6/2008 | Stone et al. | |
| 2008/0188893 A1 | 8/2008 | Selvitelli et al. | |
| 2008/0208204 A1 | 8/2008 | Schmieding et al. | |
| 2008/0208252 A1 | 8/2008 | Holmes | |
| 2008/0255557 A1 | 10/2008 | Koyfman et al. | |
| 2008/0255613 A1 | 10/2008 | Kaiser et al. | |
| 2008/0312689 A1 | 12/2008 | Denham et al. | |
| 2009/0036905 A1 | 2/2009 | Schmieding | |
| 2009/0062846 A1 | 3/2009 | Ken | |
| 2009/0062847 A1 | 3/2009 | Ken | |
| 2009/0069823 A1 | 3/2009 | Foerster et al. | |

(56) References Cited

U.S. PATENT DOCUMENTS

| | | |
|---|---|---|
| 2009/0082805 A1 | 3/2009 | Kaiser et al. |
| 2009/0187194 A1 | 7/2009 | Hamada |
| 2009/0187216 A1* | 7/2009 | Schmieding .......... A61F 2/0811 606/232 |
| 2009/0240335 A1 | 9/2009 | Arcenio et al. |
| 2009/0248068 A1 | 10/2009 | Lombardo et al. |
| 2009/0259260 A1 | 10/2009 | Bentley et al. |
| 2009/0306711 A1 | 12/2009 | Stone et al. |
| 2009/0312776 A1 | 12/2009 | Kaiser et al. |
| 2009/0318961 A1 | 12/2009 | Stone et al. |
| 2009/0326545 A1 | 12/2009 | Schaffhausen |
| 2010/0023056 A1 | 1/2010 | Johansson et al. |
| 2010/0114163 A1 | 5/2010 | Martin |
| 2010/0130989 A1 | 5/2010 | Bourque et al. |
| 2010/0145384 A1 | 6/2010 | Stone et al. |
| 2010/0211075 A1 | 8/2010 | Stone |
| 2010/0249809 A1 | 9/2010 | Singhatat et al. |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2011/0009867 A1 | 1/2011 | Oren et al. |
| 2011/0022061 A1 | 1/2011 | Orphanos et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0098727 A1 | 4/2011 | Kaiser et al. |
| 2011/0098728 A1 | 4/2011 | McDevitt et al. |
| 2011/0152885 A1 | 6/2011 | McDevitt et al. |
| 2011/0152929 A1 | 6/2011 | McDevitt et al. |
| 2011/0238111 A1 | 9/2011 | Frank |
| 2011/0264141 A1* | 10/2011 | Denham ............ A61B 17/0401 606/232 |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0116450 A1 | 5/2012 | McDevitt et al. |
| 2012/0130422 A1 | 5/2012 | Hootstein |
| 2012/0150297 A1 | 6/2012 | Denham et al. |
| 2012/0197271 A1 | 8/2012 | Astorino et al. |
| 2012/0215257 A1 | 8/2012 | McDevitt et al. |
| 2012/0239085 A1 | 9/2012 | Schlotterback et al. |
| 2012/0290004 A1 | 11/2012 | Lombardo et al. |
| 2013/0018416 A1 | 1/2013 | Lombardo et al. |
| 2013/0023930 A1 | 1/2013 | Stone et al. |
| 2013/0035722 A1 | 2/2013 | McDevitt et al. |
| 2013/0110165 A1 | 5/2013 | Burkhart et al. |
| 2013/0123810 A1 | 5/2013 | Brown et al. |
| 2013/0123813 A1 | 5/2013 | Stone et al. |
| 2013/0138123 A1 | 5/2013 | Stone et al. |
| 2013/0158601 A1 | 6/2013 | Stone et al. |
| 2013/0178901 A1 | 7/2013 | Arai et al. |
| 2013/0237997 A1 | 9/2013 | Arai et al. |
| 2013/0296934 A1 | 11/2013 | Sengun |
| 2013/0345748 A1 | 12/2013 | Dreyfuss |
| 2014/0052178 A1 | 2/2014 | Dooney, Jr. |
| 2014/0052179 A1 | 2/2014 | Dreyfuss et al. |
| 2014/0114330 A1 | 4/2014 | Karasic et al. |

FOREIGN PATENT DOCUMENTS

| | | |
|---|---|---|
| EP | 0684013 | 11/1995 |
| EP | 1917915 | 5/2008 |
| EP | 2277456 | 1/2011 |
| EP | 2606833 | 6/2013 |
| EP | 2749230 | 2/2014 |
| FR | 2743294 | 7/1997 |
| GB | 2370227 | 6/2002 |
| JP | H08-052155 | 2/1996 |
| JP | 2006-503655 | 2/2006 |
| JP | 2010-500912 | 1/2010 |
| JP | 2010-537746 | 12/2010 |
| JP | 2011-025036 | 2/2011 |
| WO | 2003092551 | 11/2003 |
| WO | 2004037094 | 5/2004 |
| WO | 2006023793 | 3/2006 |
| WO | 2006086275 | 8/2006 |
| WO | 2007005394 | 1/2007 |
| WO | 2007037326 | 4/2007 |
| WO | 2008022250 | 2/2008 |
| WO | 2008137197 | 11/2008 |
| WO | 2009029914 | 3/2009 |
| WO | 2009052294 | 4/2009 |
| WO | 2012048050 | 4/2012 |
| WO | 2012103536 | 8/2012 |
| WO | 2012112793 | 8/2012 |
| WO | 2013134277 | 9/2013 |
| WO | 2014062684 | 4/2014 |

OTHER PUBLICATIONS

"Endobutton Direct: Fixation Device," Smith & Nephew, Inc., reprinted from http://global.smith-nephew.com/us/ product23376_5895.htm, on Nov. 22, 2010, 3 pages.
"Endobutton CL," Smith and Nephew, Inc., reprinted from http://endo.smith-nephew.com/es/Standard.asp? NodeID=2715, on Nov. 22, 2010, 1 page.
"ToggleLOC: Femoral Fixation Device with Zip Loop Technology," Biomet Sports Medicine. Inc., 2007, 8 pages.
Scope This Out, vol. 10, No. 2, Summer 2008, 8 pages.
Scope This Out, vol. 12, No. 2, Fall 2010, 8 pages.
Scope this Out, vol. 12, No. 1, Spring 2010, 8 pages.
"Shoulder Restoration System: Y-Knot™ 1.3mm All-Suture Anchor," ConMed™ Linvatec, 2011, 4 pages.
"Shoulder Restoration System: Arthroscopic Bankart Repair Using the Y-Knot™ 1.3mm All-Suture Anchor," ConMed™ Linvatec, 2011, 4 pages.
"Game Plan: Innovative Products to be Launched AAOS 2010," Biomet Sports Medicine, Spring 2010, vol. 2, No. 3, 1 page.
From, Stuart, "AGL Reconstruction with Bone-Tendon-Bone Transplants using the Endobutton CL BTB Fixation System," Smith & Nephew, Inc., ©2004, printed on Apr. 4, 11 pages.
Glousman, R., et al., "JuggerKnot Soft Anchor Surgical Technique," Biomet Sports Medicine, 2010, 1 page.
Lawhorn, K., "MaxFire MarXmen Device Surgical Technique," Biomet Sports Medicine, 2010, 1 page.

* cited by examiner

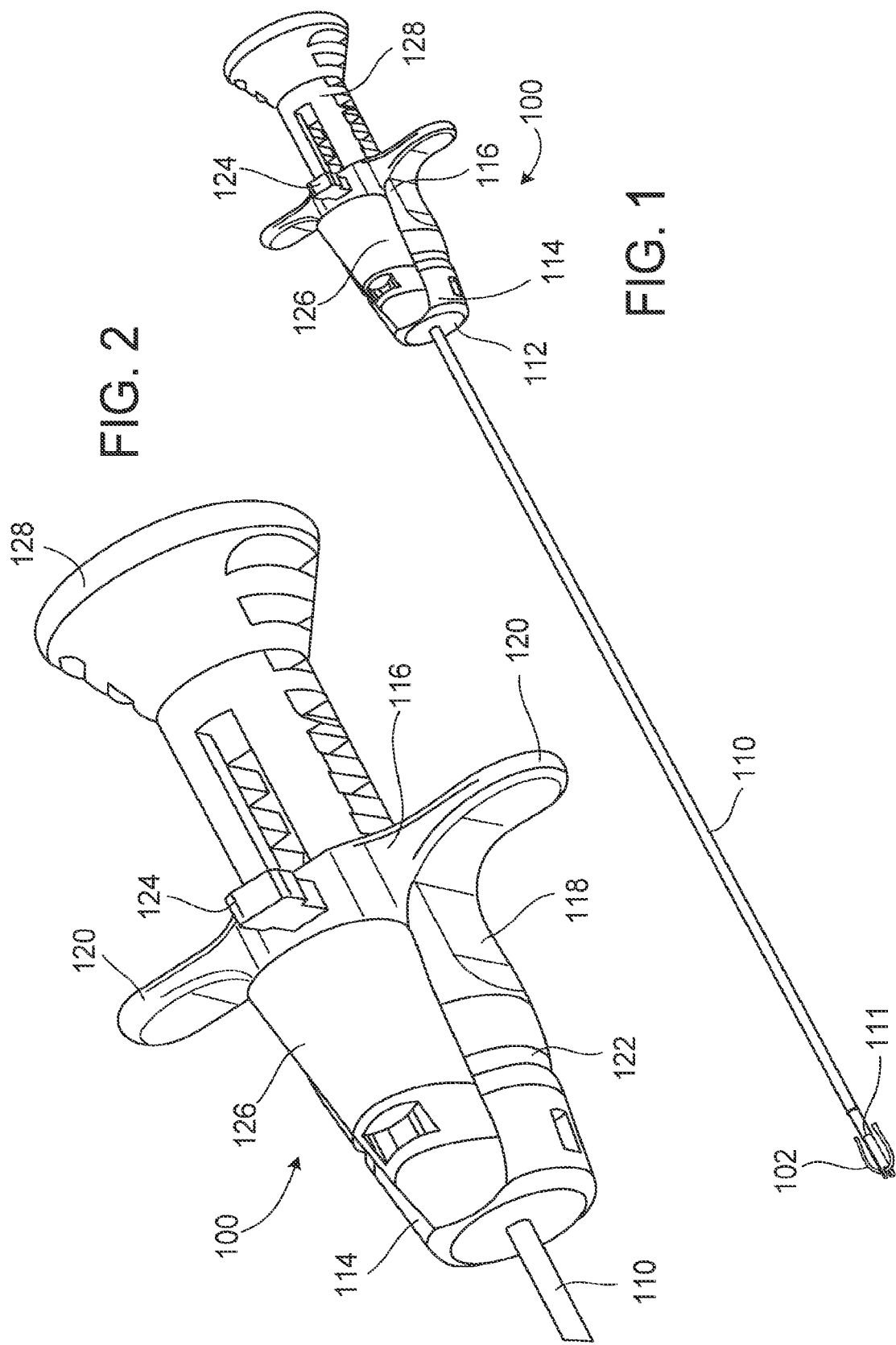

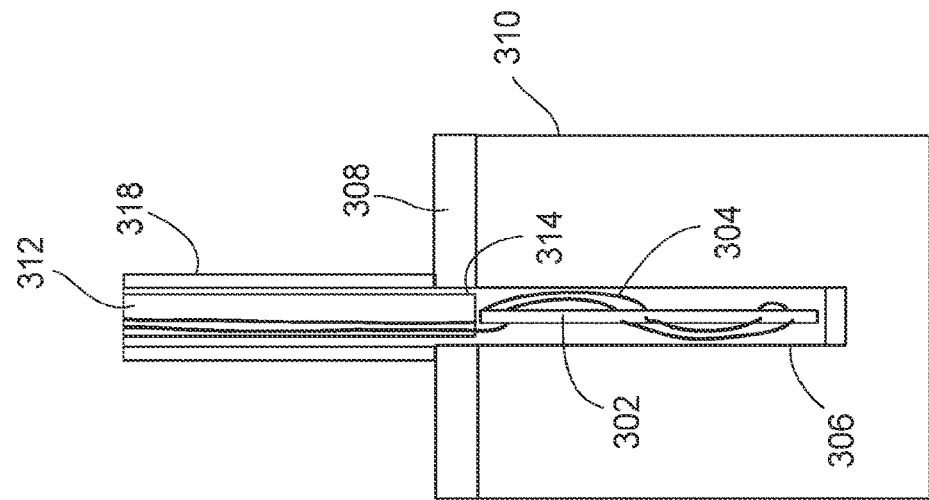
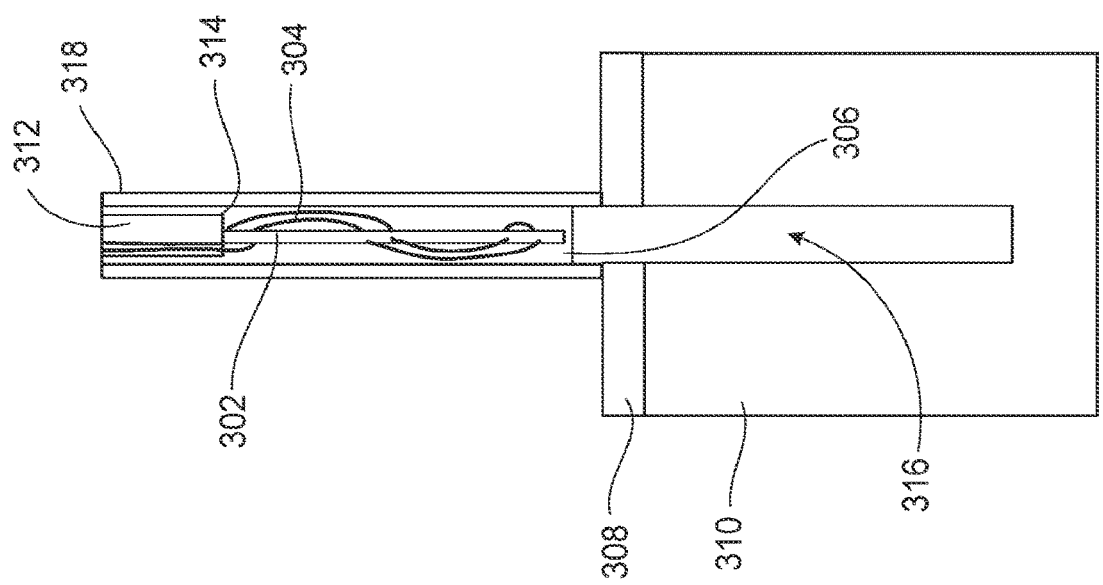

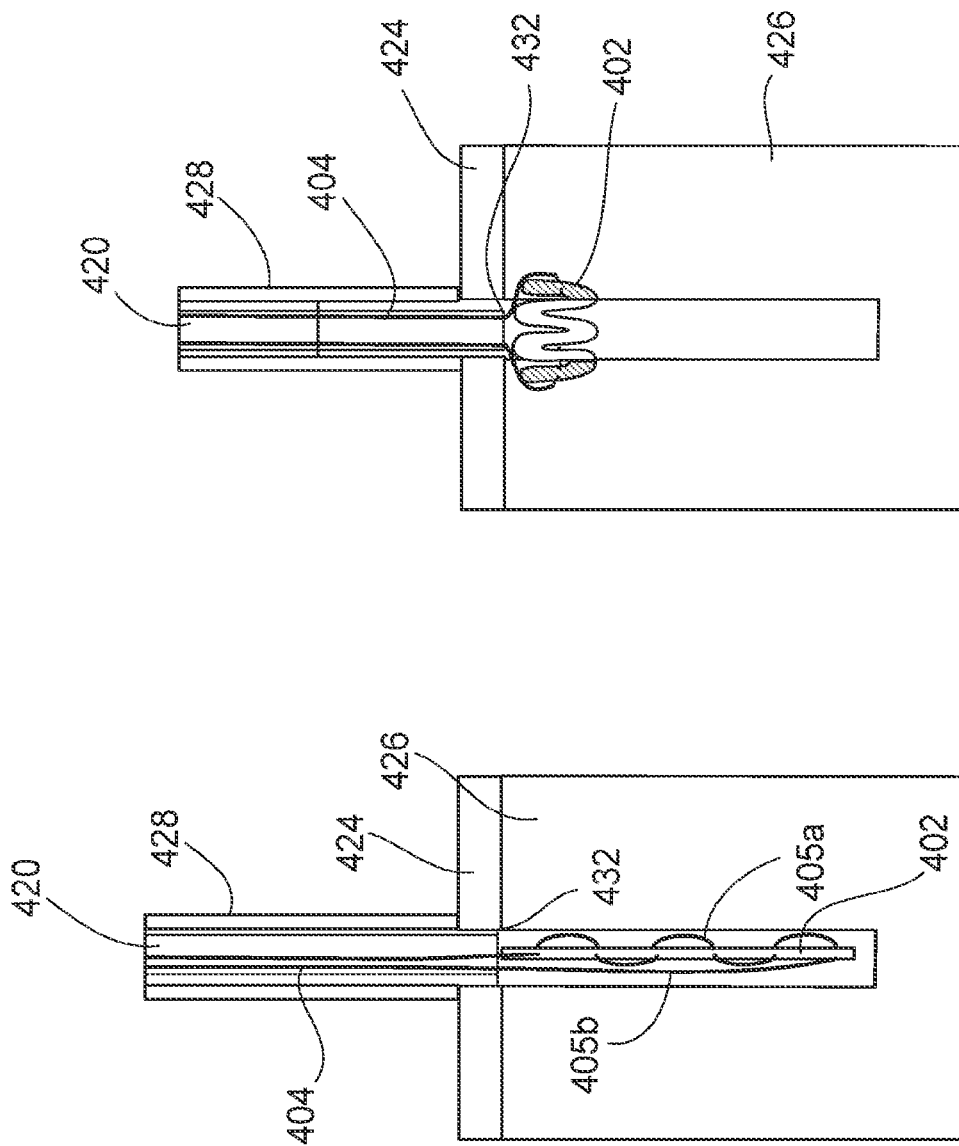

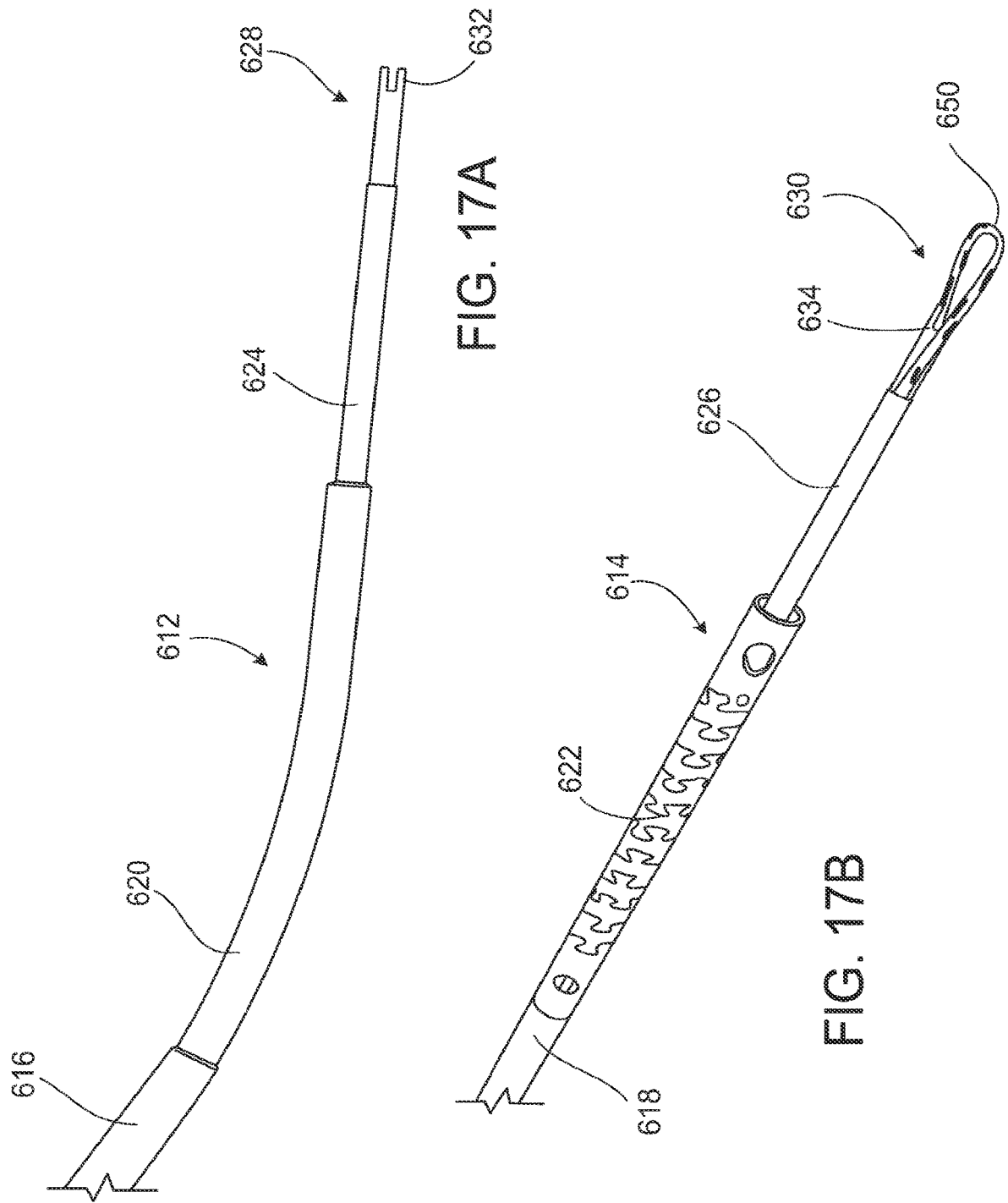

FLEXIBLE ANCHOR DELIVERY SYSTEM

CROSS-REFERENCE TO RELATED APPLICATIONS

This application is a continuation of co-pending U.S. application Ser. No. 17/114,585, filed Dec. 8, 2020, entitled FLEXIBLE ANCHOR DELIVERY SYSTEM, now U.S. Pat. No. 11,723,650, which in turn is a continuation of U.S. application Ser. No. 16/684,713, filed Nov. 15, 2019, now U.S. Pat. No. 11,607,211, which in turn is a continuation of U.S. application Ser. No. 16/373,090, filed Apr. 2, 2019, now U.S. Pat. No. 10,617,408, which in turn is a continuation of U.S. application Ser. No. 16/000,980, filed Jun. 6, 2018, now U.S. Pat. No. 10,292,697, which in turn is a continuation of U.S. application Ser. No. 14/433,684, filed Apr. 6, 2015, now U.S. Pat. No. 10,010,314, which in turn is a U.S. national phase entry under 35 U.S.C. § 371 of International Application No. PCT/US13/65064, filed Oct. 15, 2013, which in turn is a continuation of U.S. application Ser. No. 13/654,855, filed Oct. 18, 2012, now U.S. Pat. No. 8,986,327, the contents of which are incorporated herein by reference in their entirety for all purposes.

TECHNICAL FIELD

This disclosure relates to apparatus and methods for repairing tissue.

BACKGROUND

Arthroscopic procedures using sutures and suture anchors have been used in tissue repair to, for example, secure soft tissue to bone. These anchors may not fully deploy below the cortical layer. An anchor that is not fully deployed at the time of installation does not provide maximum fixation and could migrate later causing the repair suture to loosen, sacrificing the integrity of the repair. An anchor not providing its maximum fixation may result in pull out during or after the repair procedure. Anchors may also be damaged during insertion. Fraying of the anchor and repair sutures, or other damage, may result in a number of problems including compromised anchor construct, anchor severing, repair suture severing, the repair suture pulling through the anchor, etc.

SUMMARY

The details of one or more implementations of the disclosure are set forth in the accompanying drawings and the description below. Other features and advantages will be apparent from the description and drawings, and from the claims.

In one aspect, an assembly includes a flexible fixation member, a suture, and a delivery device. The flexible fixation member includes a body with two terminal ends. A suture passes through the flexible fixation member at various points along a length of the body between the terminal ends such that portions of the fixation member are slidable relative to the suture and configurable to form a cluster within a surgical site. The delivery device includes a tubular member, an elongated inserter, and a trigger. The elongated inserter is slidably disposed within the tubular member. The inserter has a forked distal end and a proximal end, the forked distal end is configured to receive a portion of the flexible fixation member and the suture. The trigger is finger-engagable and is fixedly coupled to the proximal end of the inserter. It is configured to advance and retract the inserter relative to the tubular member. The trigger includes a retention member for retaining a proximal end portion of the suture.

Implementations may include one or more of the following. For example, the delivery device may further include a handle to which the trigger is slidably coupled. The delivery device may further include a button coupled to the trigger and the handle and configured to permit the trigger to slide relative to the handle when the button is depressed. The handle may define a plurality of cutout portions along a length of the handle. The cutout portions are configured to receive a portion of the button therein to fixedly engage the trigger to the handle. The trigger may further include a circumferential groove defined about a periphery of the trigger. A length of the suture may be wrapped about trigger at least once and retained in the groove. The trigger may define a slot configured to receive a portion of the suture therethrough and direct the suture into the groove. The trigger may have a substantially cylindrical body and a pair of finger-engagable elements extending laterally from the body. The delivery device may also include a cover disposed over the retention member. The handle may define two openings in a distal end of the handle, a first opening positioned distally with respect to a second opening, such that the suture passes from an interior to an exterior of the handle through the first of the two openings and the suture passes from the exterior to the interior of the handle through the second of the two openings. The handle may define two openings in a distal end of the handle, a first opening positioned distally with respect to a second opening, such that the suture passes from an interior to an exterior of the handle through the second of the two openings and the suture passes from the exterior to the interior of the handle through the first of the two openings. The handle may define an opening in a distal end of the handle, such that the suture passes from an interior to an exterior of the handle through the opening. The delivery device may further include a cover element releasably coupled to a distal end of the handle and fixed coupled to a proximal end of the tubular member. The suture may pass through the fixation member to form two substantially parallel tail sections of suture. The fixation member may be non-tubular. The flexible fixation member and the suture may comprise a size 2 suture.

In another aspect, a method of closing a tissue wound, includes delivering a wound closure assembly to a surgical site, advancing an inserter distally relative to a tubular member to position the flexible fixation member within a targeted tissue site, tensioning a suture to form a cluster of the portions of the fixation member within the surgical site, and retracting the inserter proximally relative to the tubular member to remove the forked distal end of the inserter from within the targeted tissue site. The wound closure assembly including a flexible fixation member, a suture, and a delivery device. The flexible fixation member includes a body having two terminal ends. The suture passes through the flexible fixation member at various points along a length of the body between the terminal ends such that portions of the fixation member are slidable relative to the suture and configurable to form a cluster within a surgical site. The delivery device has a tubular member, an elongated inserter slidably disposed within the tubular member, and a finger-engagable trigger. The inserter has a forked distal end, configured to receive a portion of the flexible fixation member and the suture therein. The finger-engagable trigger is fixedly coupled to the proximal end of the inserter and configured to advance and retract the inserter relative to the tubular member. The trigger comprises a retention member for retaining a proximal end portion of the suture.

Implementations may include one or more of the following. For example, tensioning the suture to form the cluster of the portions of the fixation member with the surgical site may include pulling the fixation member against a distal end of the tubular member. Tensioning the suture may be carried out by moving the trigger in a proximal direction relative to the tubular member. Retracting the inserter may be carried out by moving the trigger in a proximal direction relative to the tubular member. Tensioning the suture and retracting the inserter are carried out by moving the trigger in a proximal direction relative to the tubular member such that the forked end of the inserter is moved proximally over a distance before tensioning of the suture begins. The method may further include drilling a hole into the tissue.

DESCRIPTION OF THE DRAWINGS

FIG. 1 is a perspective view of a delivery device.

FIG. 2 is a perspective view of a proximal portion of the delivery device of FIG. 1.

FIGS. 13B-13E illustrate the method of use of the distal end of a delivery device with the flexible fixation member and suture assembly of FIG. 13a.

FIGS. 14A-14D illustrate the method of use of the distal end of a delivery device with another flexible fixation member and suture assembly.

FIGS. 17A-17E are perspective views of a flexible delivery device.

DETAILED DESCRIPTION

Figure 8:
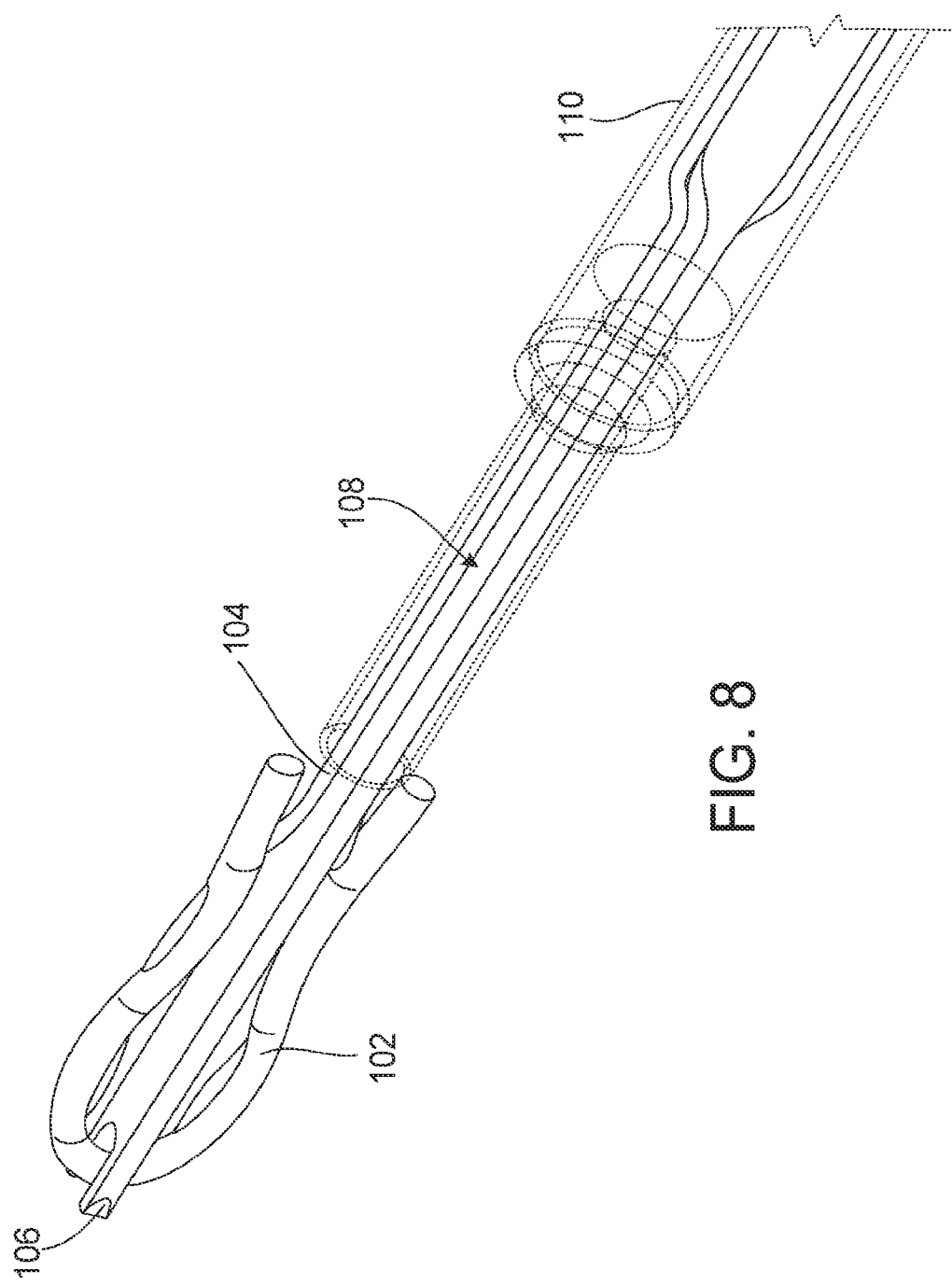

FIG. 1 shows a surgical device 100 used for delivering one or more fixation members to a surgical site. The device 100 includes a handle 128, a trigger 116 movable coupled to the handle 128, a cover element 114 coupled to the trigger 116, a tubular member 110 attached to the cover element 114, and fixation member or anchor 102 having a flexible member or suture 104 (FIG. 8) interwoven through the fixation member 102. The fixation member 102 and suture 104 are disposed in a distal end 106 of an elongated inserter 108 (FIG. 8). The elongated inserter 108 is slidably positioned within the tubular member 110. The proximal end 112 of tubular member 110 is coupled to the cover element 114. The proximal end of the delivery device 100 is shown in more detail in FIG. 2. The cover element 114 is coupled to a cover 126 and the trigger 116. The trigger 116 includes a body 118, finger engagable elements 120 extending generally perpendicular from a longitudinal axis of the body 118, a circumferential groove 122, and a button 124. The trigger 116 is movably coupled to the handle 128. The button 124 interacts with cutout portions 130 (FIG. 3) in the handle 128 to lock the motion of the trigger 116 with respect to the handle 128. The button 124 can be depressed, which eliminates the interference between the button 124 and the cutouts 130 allowing motion of the trigger 116 with respect to the handle 128.

Figure 3A:
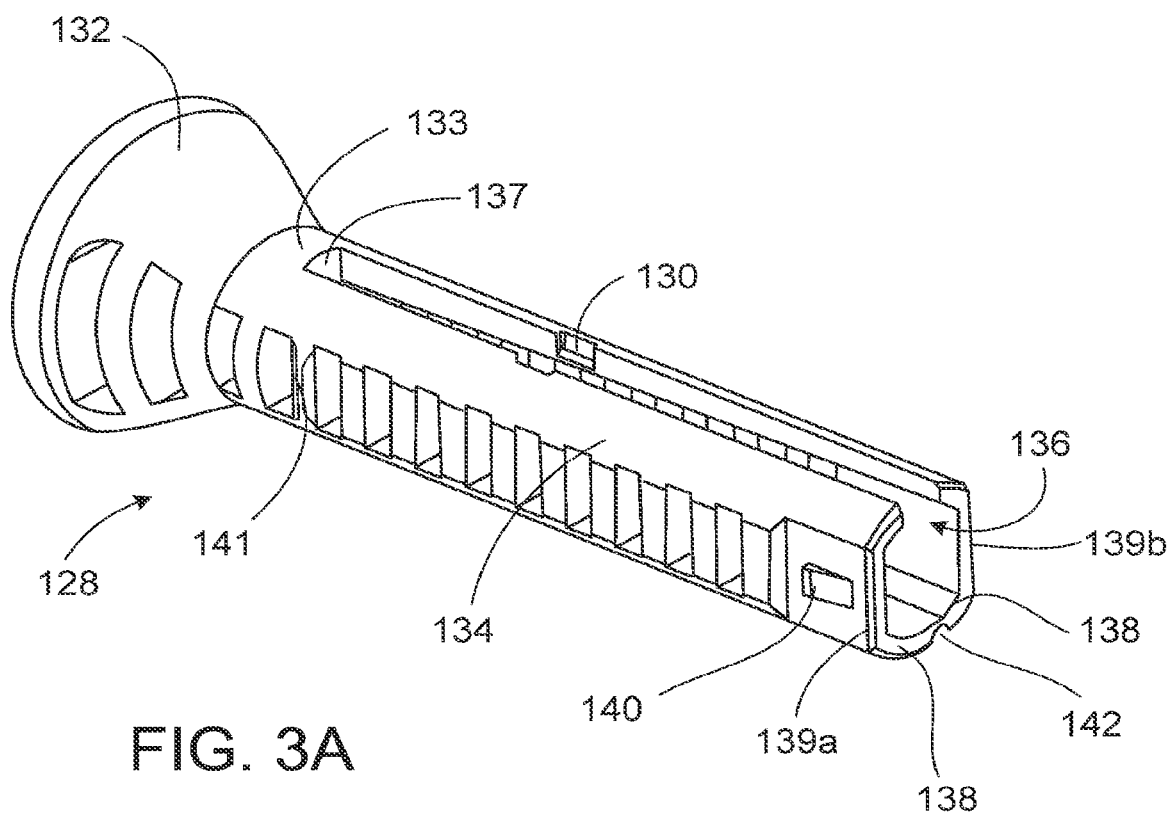
FIGS. 3A and 3B are perspective views of a handle of the delivery device of FIG. 1.
Figure 3B:
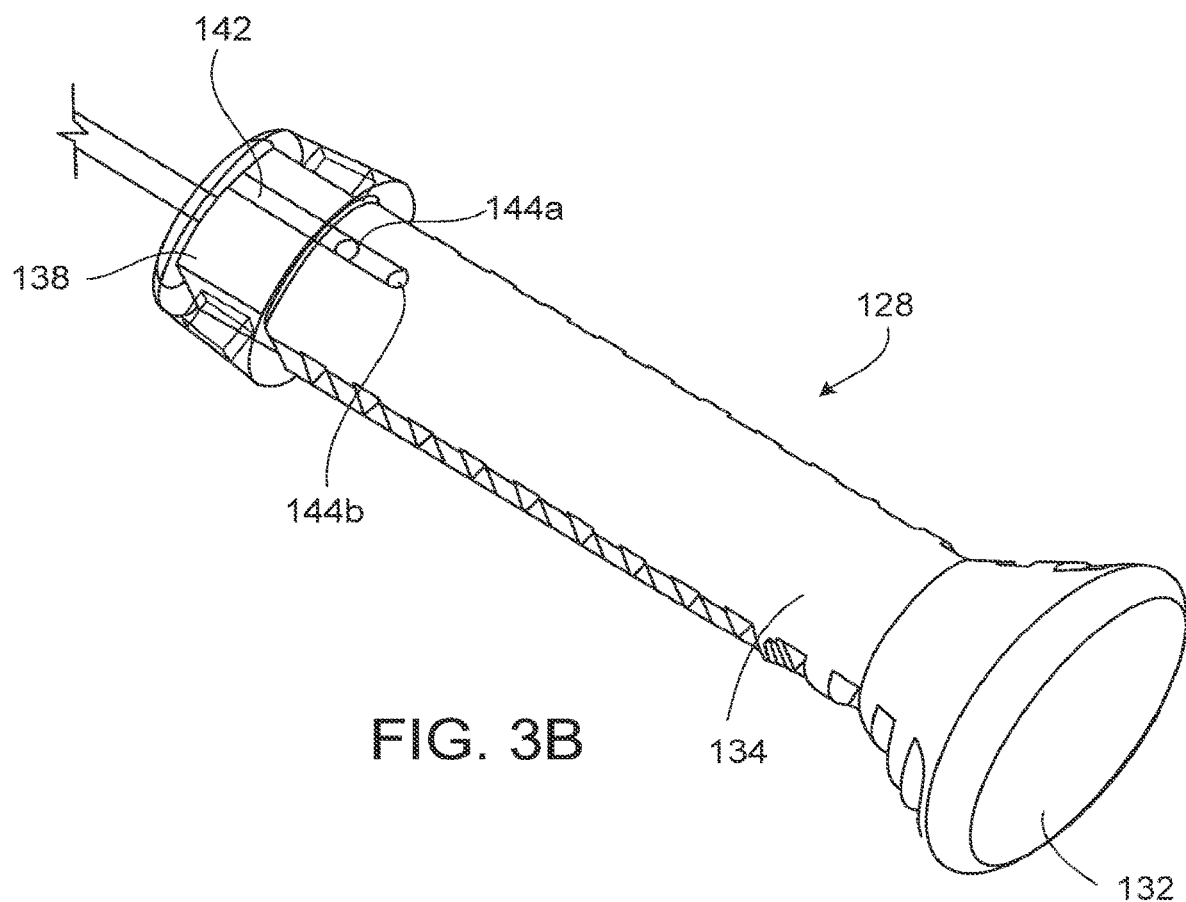

Referring to FIGS. 3A and 3B, the handle 128 includes an enlarged proximal end 132 that may enhance a user's grip on the handle 128. The proximal end 132 is connected to or formed integral with a hollow elongated body 134. The body 134 includes a longitudinal slot 136 extending from a distal end 138 at least partially toward the proximal end 132. One of the enlarged proximal end 132 or the proximal wall 137 of the slot 136 may act as a stop for the trigger 116. Distal end 138 also includes two straight portions 139a and 139b. Cut out portions 130 are provided along the slot 136 and are sized to receive a portion of the button 124. The distal end 138 includes mating features 140 to couple with the cover element 114. The proximal end 133 of the body 134 includes a protrusion 141 which interacts with the trigger 116 to act as a detent for the trigger 116 in the deployed orientation. The interaction of protrusions 141 and the trigger 116 may also create an audible click or sound. Groove 142 and openings 144a, 144b in the distal end 138 of the handle 128 allow for routing of the suture 104 as will be explained in more detail below.

Figure 4A:
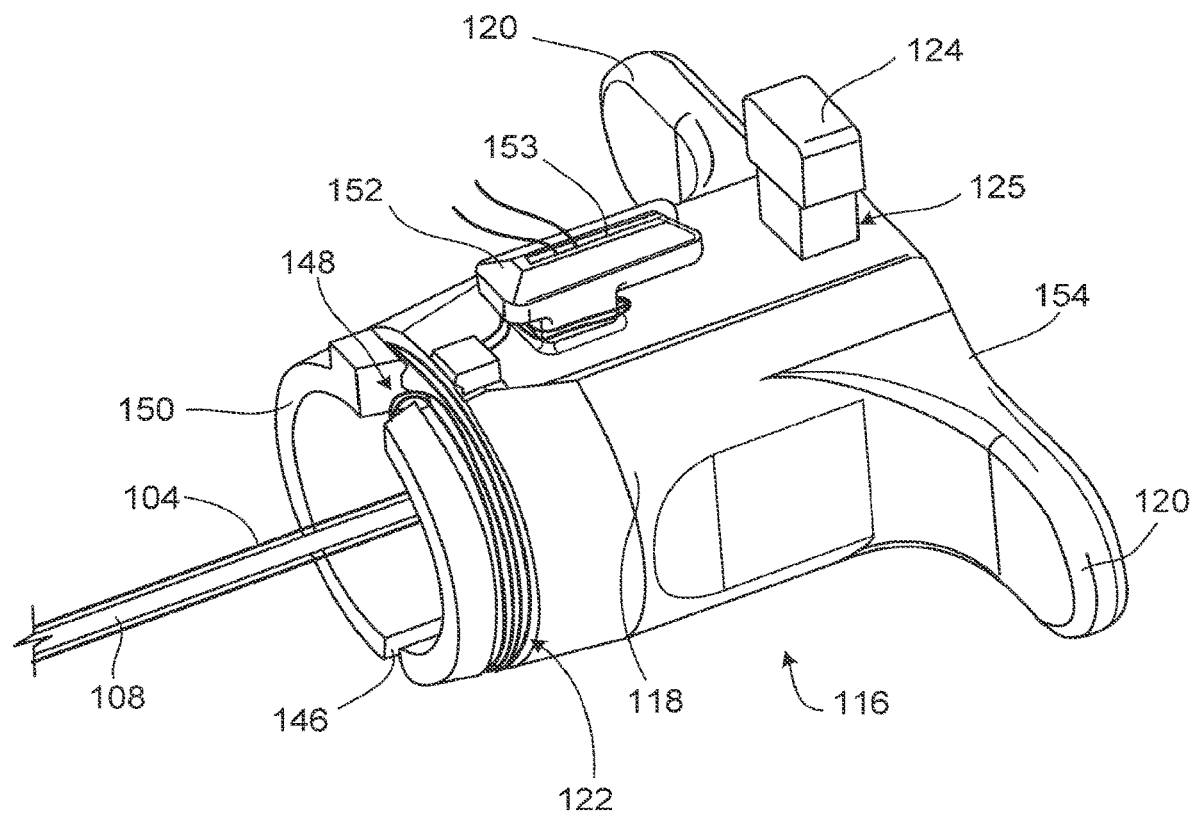
FIGS. 4B-4D are perspective views of a partial assembly of the proximal portion of the delivery device of FIG. 1 including the trigger of FIG. 4A.
FIG. 4E is a cutaway view of a partial assembly of the proximal portion of the delivery device of FIG. 1.
FIGS. 4F-4H are cutaway views of embodiments of the delivery device of FIG. 1 with different suture routing pathways within the handle.
Figure 4B:
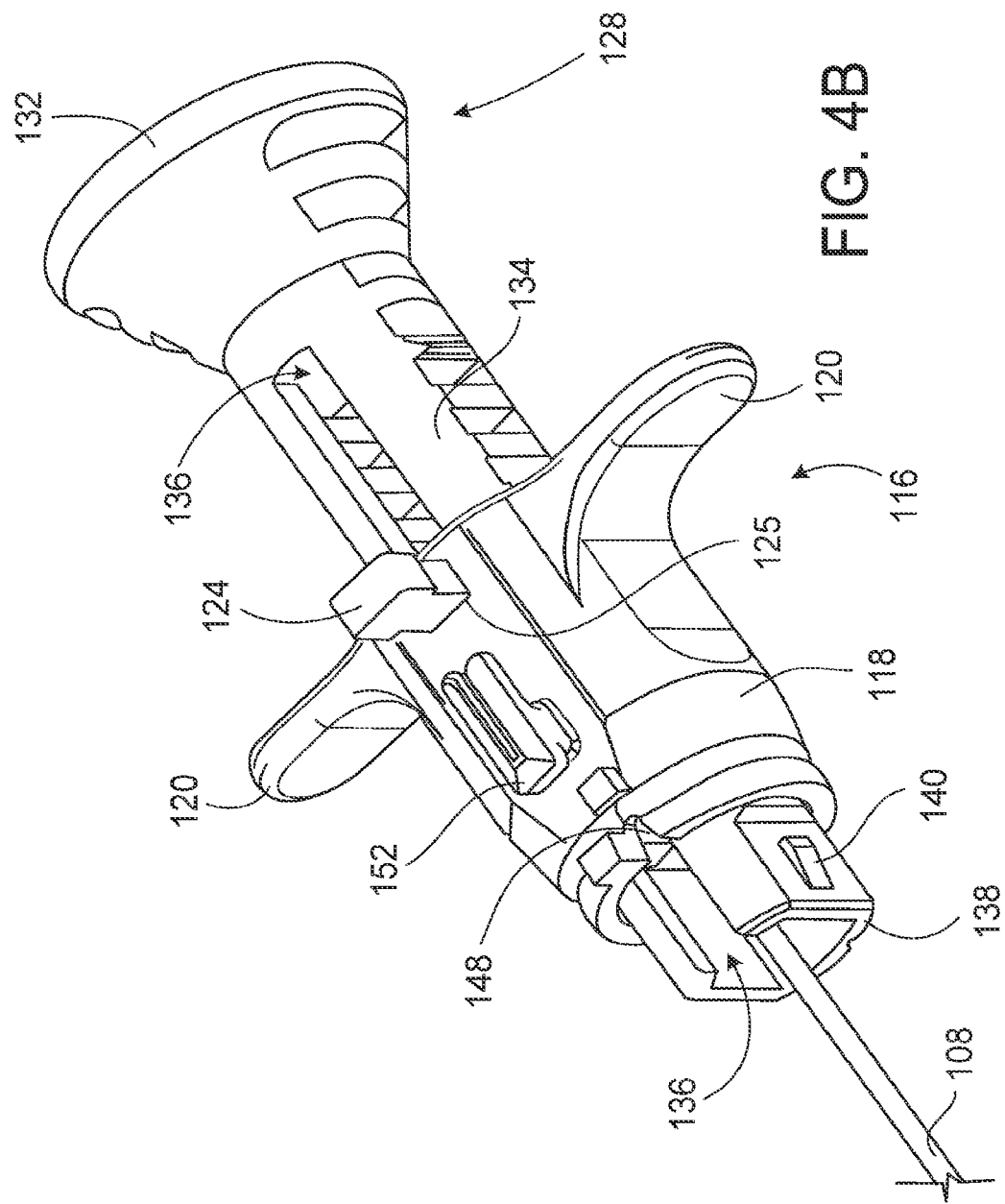
Figure 4C:
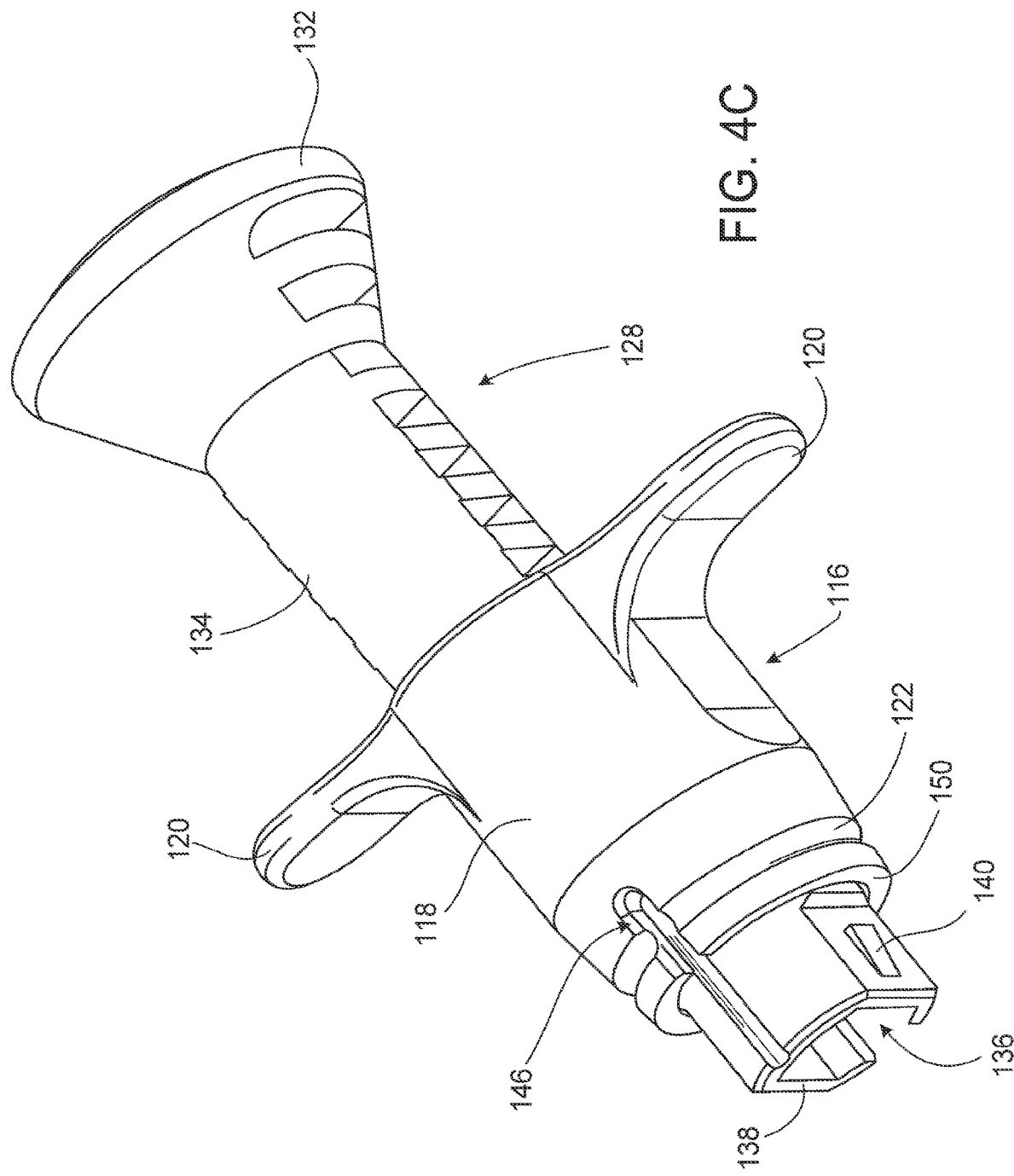

The trigger 116, shown in FIG. 4A, includes two finger engagable elements 120 protruding from either side of the body 118. The finger engagable elements 120 are designed to be grasped by a surgeon's fingers while the device is being operated, as described in more detail below. Slots 146 and 148 extend from the distal end 150 of the trigger 116 and may be in contact with the groove 122. The slot 148 and the groove 122 are designed for routing of the suture 104 as shown. The groove 122 runs circumferentially around the trigger's body 118 and allows for longer sutures to be wrapped around it, increasing the length of suture that can be used with the delivery device 100. Trigger 116 also includes a retention member 152 with a slot 153 which is used to cleat sutures 104 to keep them in place. Button 124 fits in a rectangular cutout 125 in the proximal end 154 of the trigger 116. In its upright position, the button 124 engages cutout portions 130 of the handle 128 (FIG. 3A) and prevents the trigger 116 from moving with respect to the handle 128. When the button 124 is depressed, the trigger 116 is free to slide up and down the body 134 of the handle 128.

FIGS. 4B-4E show the trigger 116, handle, 128, and elongated inserter 108 in an assembled configuration. The elongated inserter 108 is attached to a tongue 156 of the trigger 116 by, for example, insert molding, friction fit, welding or some other suitable attachment means, such that the elongated inserter 108 moves with the trigger 116. The proximal end of the elongated inserter 108 has reliefs 172 (FIG. 6) to prevent the inserter 108 from pushing through the tongue 156 in the trigger 116. The tongue 156 of the trigger 116 fits through the slot 136 and within the hollow portion of the body 134 of the handle 128, while the body 118 of the trigger 116 is slidingly coupled to the body 134 of the handle 128. The mating features 158 of the button 124 may engage the cutout portions 130 of the handle 128, when the button is in its upright position (FIG. 4E) to prevent the trigger 116 from moving with respect to the handle 128. The trigger 116 may be injection molded and made of ABS. The trigger 116 and the handle 128 are made of dissimilar materials to reduce the friction between the two which allows the trigger to slide along the body 134 of the handle more easily.

Figure 4D:
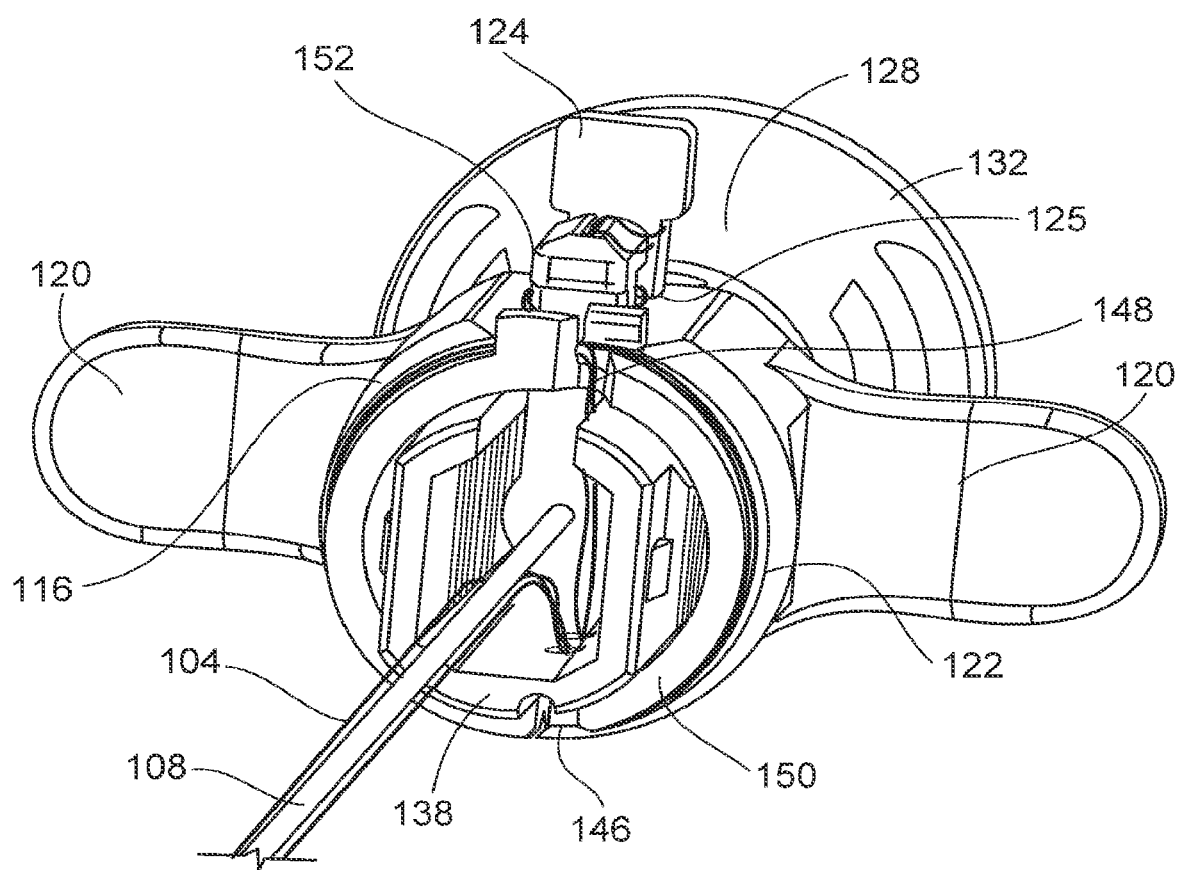
Figure 4E:
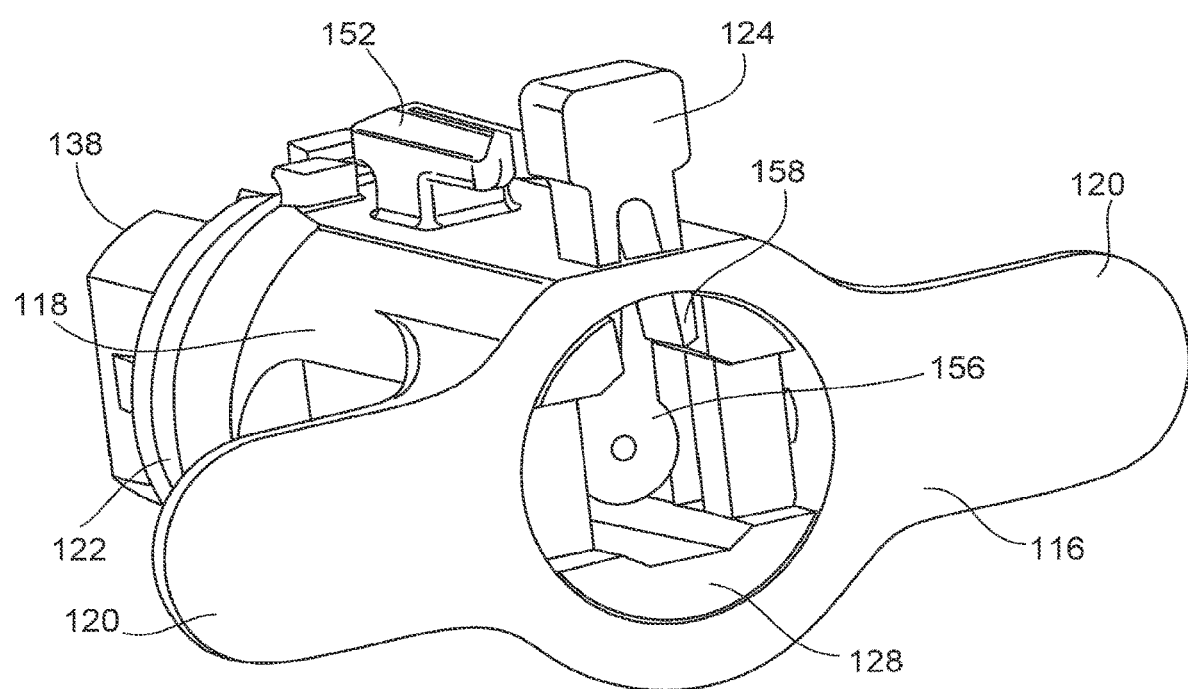
Figure 4F:
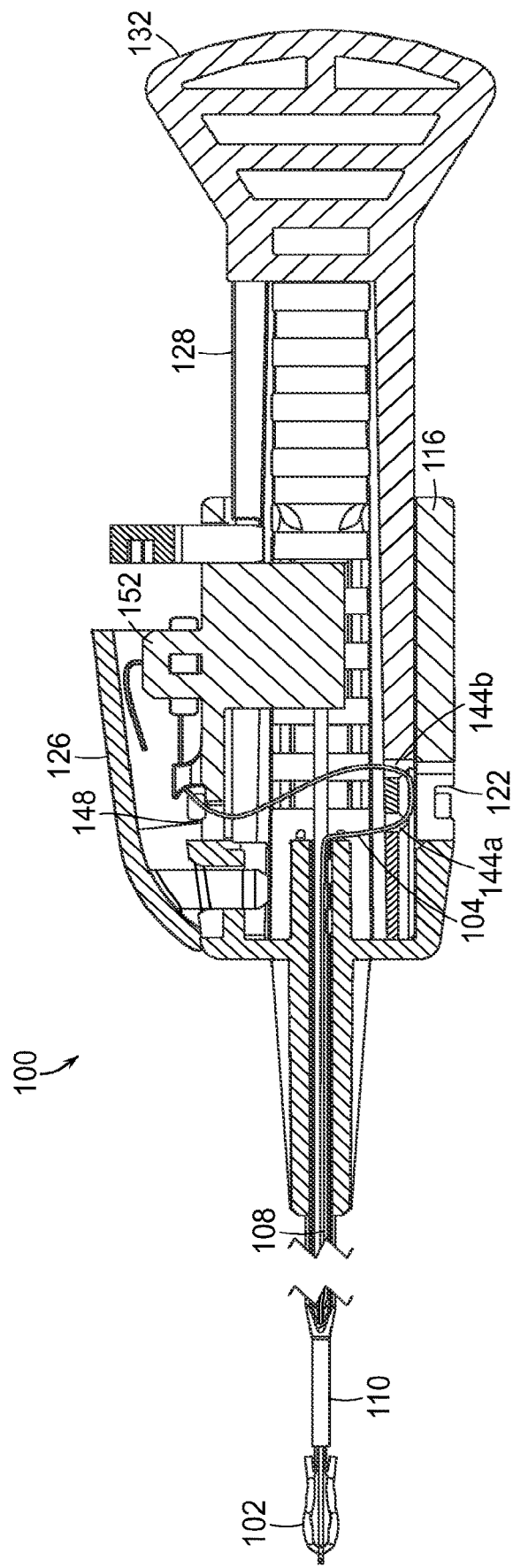

As shown in FIGS. 4A, 4D, and 4F, the suture 104 travels down the elongated inserter 108, is routed out of the handle 128 through hole 144a, and then back through hole 144b before passing out of slot 148 and wrapping around trigger 116. Some slack is left in the suture 104. The ends of the suture 104 can be secured in the slot 153 on the retention member 152.

In alternative embodiments, the tension within the suture 104 may be varied by changing the routing path of the suture 104 within the handle 128. As discussed in greater detail below, the ability to variably tension the suture 104 may facilitate fixation of the flexible fixation member 102 in bone. For example, decreasing the path length of the suture 104, as compared to the routing path illustrated in FIGS. 4A, 4D, and 4F, may increase the tension of the suture 104.

Figure 4G:
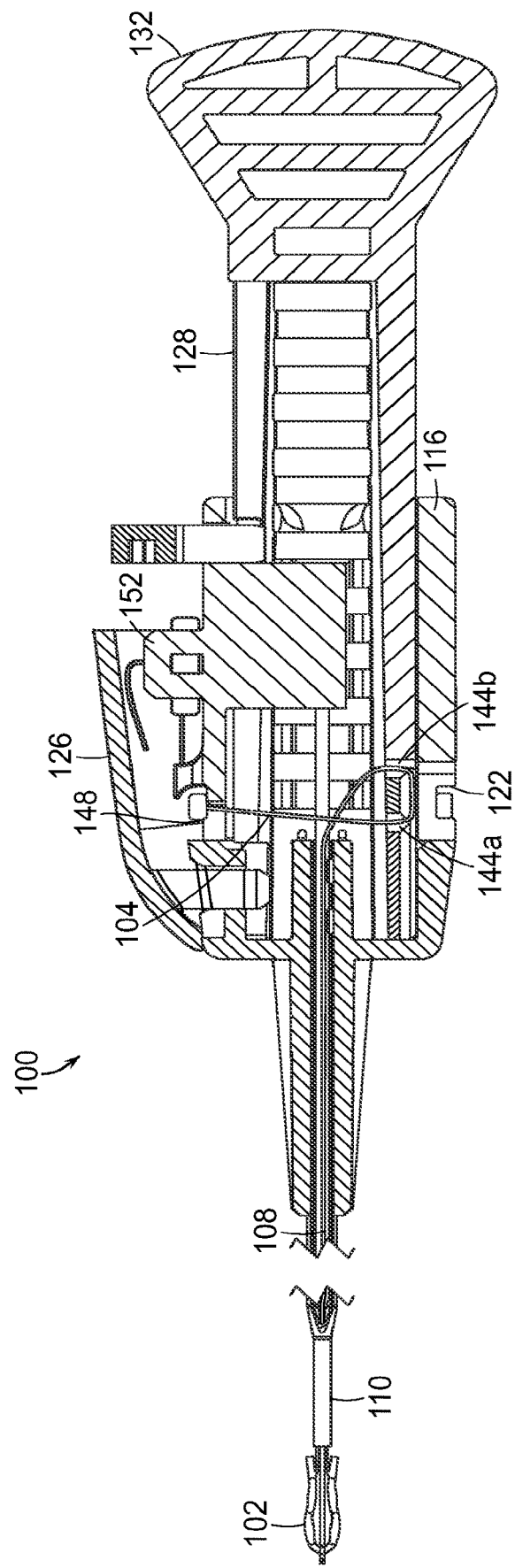

FIG. 4G illustrates one embodiment of a suture routing path which increases the suture tension, as compared to the routing path of FIGS. 4A, 4D, and 4F. The suture 104 travels down the elongated inserter 108 and is routed out of the handle 128 through hole 144b and then back through hole 144a before passing out of the slot 148 and wrapping around trigger 116. Less slack is left in the suture 104, as compared to suture routing path illustrated FIGS. 4A, 4D, and 4F. The ends of the suture 104 can be secured in the slot 153 on the retention member 152.

Figure 4H:
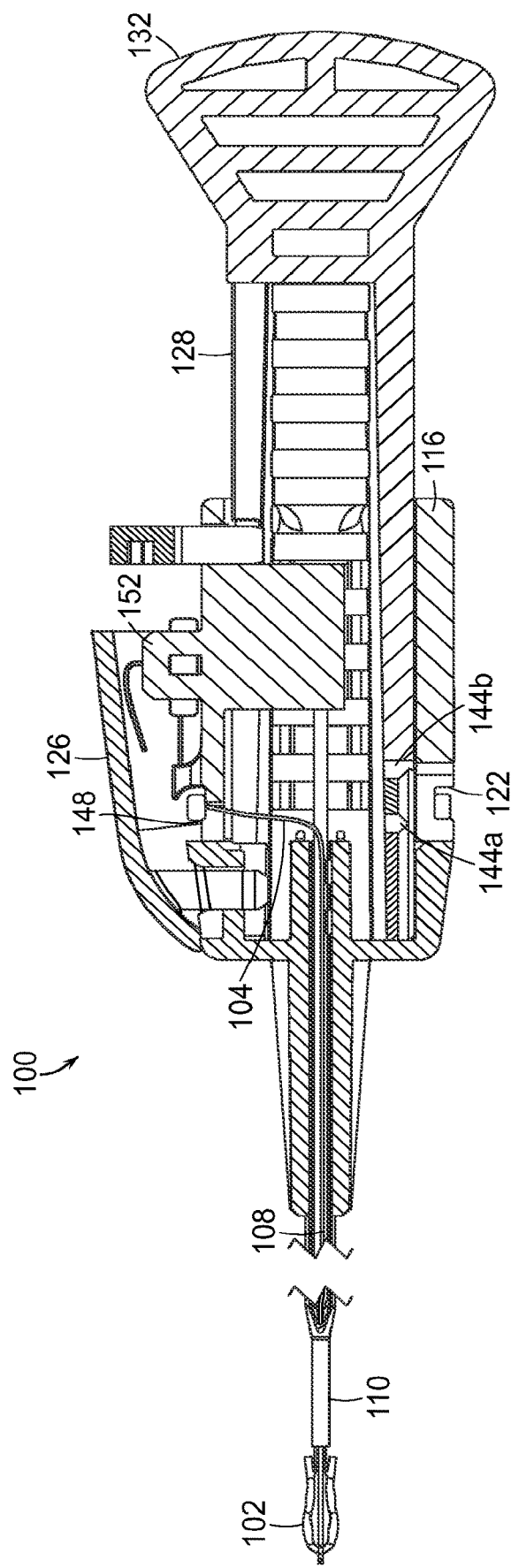

FIG. 4H illustrates another embodiment of a suture routing path which further increases the suture tension, as compared to the routing path of FIG. 4G. In contrast to the embodiments above, the suture 104 is not routed out of the handle 128 through either hole 144b or hole 144a before passing out of the slot 148. Instead, the suture 104 travels down the elongated inserter 108, passes out of the slot 148, and wraps around trigger 116. Relatively little slack is left in the suture 104, as compared to the routing pathways of FIG. 4A, 4D, 4F, or 4G. The ends of the suture 104 can be secured in the slot 153 on the retention member 152.

Figure 5A:
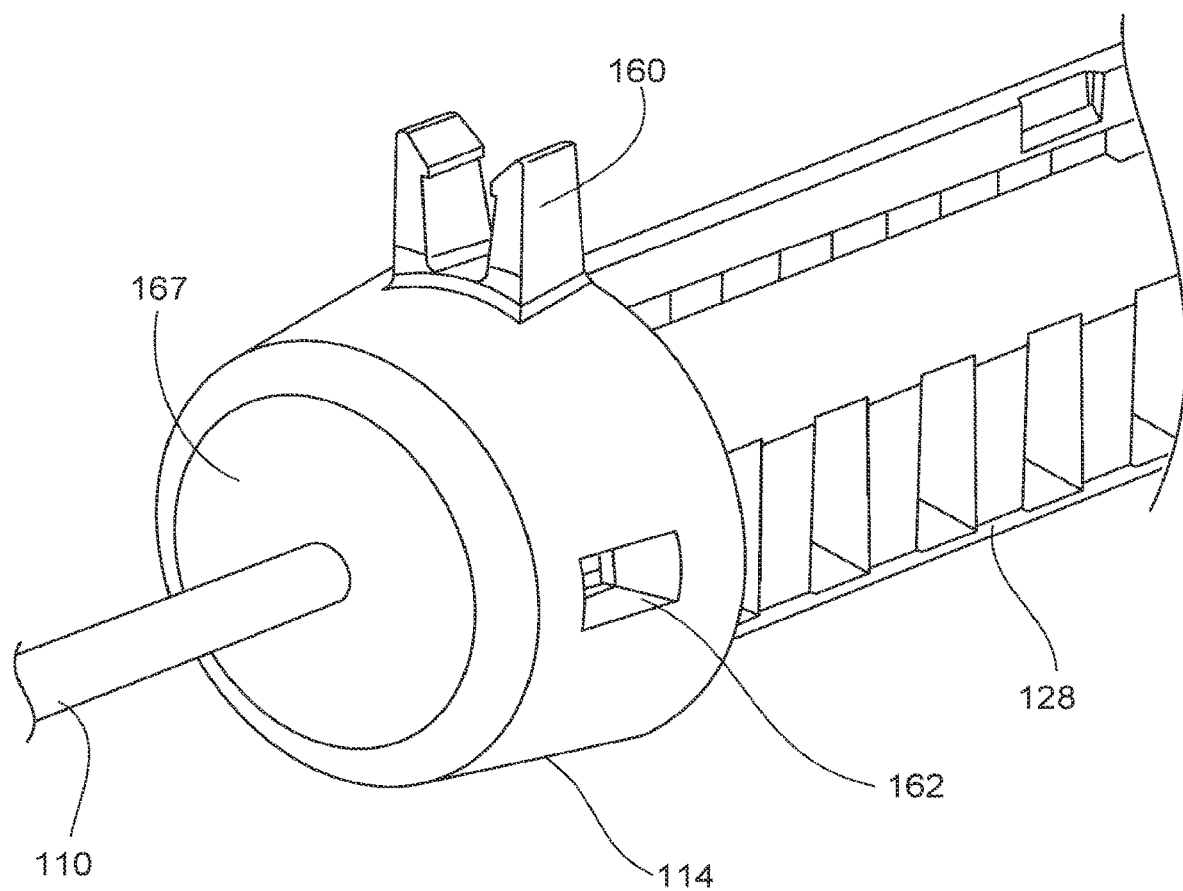
FIGS. 5A and 5B are perspective views of a partial assembly of the proximal portion of the delivery device of FIG. 1 including a cover element and tubular member.
Figure 5B:
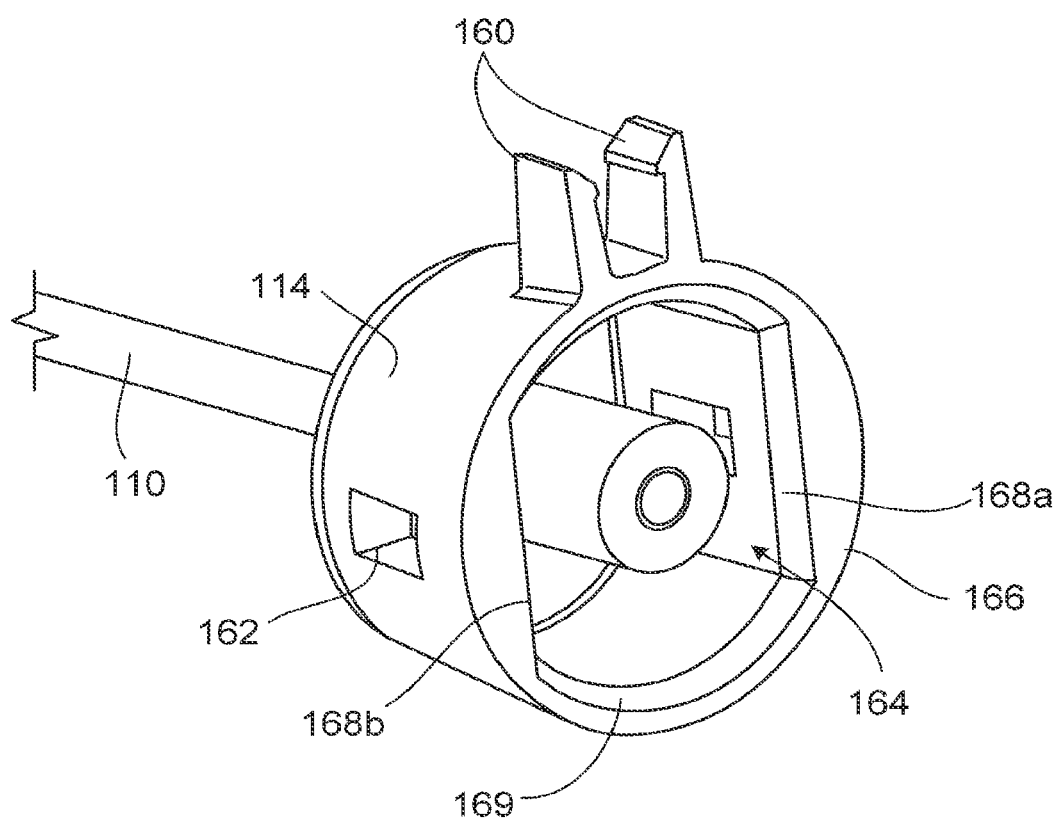

Referring to FIGS. 5A and 5B, the cover element 114 is coupled to the tubular member 110 by; for example, insert molding, welding, friction fit, or other suitable means. The cover element 114 also includes mating features 162 to engage mating features 140 of the handle 128 (FIGS. 3A and 3B), and mating feature 160 to engage the cover 126 (FIG. 1). A hollow cavity 164 extends from the proximal end 166 of the cover element 114 towards its distal end 167. The hollow cavity 164 has two straight portions 168a, 168b which engage straight portions 139a, 139b of the handle 128 and allow the handle 128 and cover element 114 to rotate together, but limit the handle 128 and cover element 114 from rotating relative to each other. The edges of the hollow cavity 164 have a chamfer 169 to provide lead-in for ease of assembly.

Figure 6:
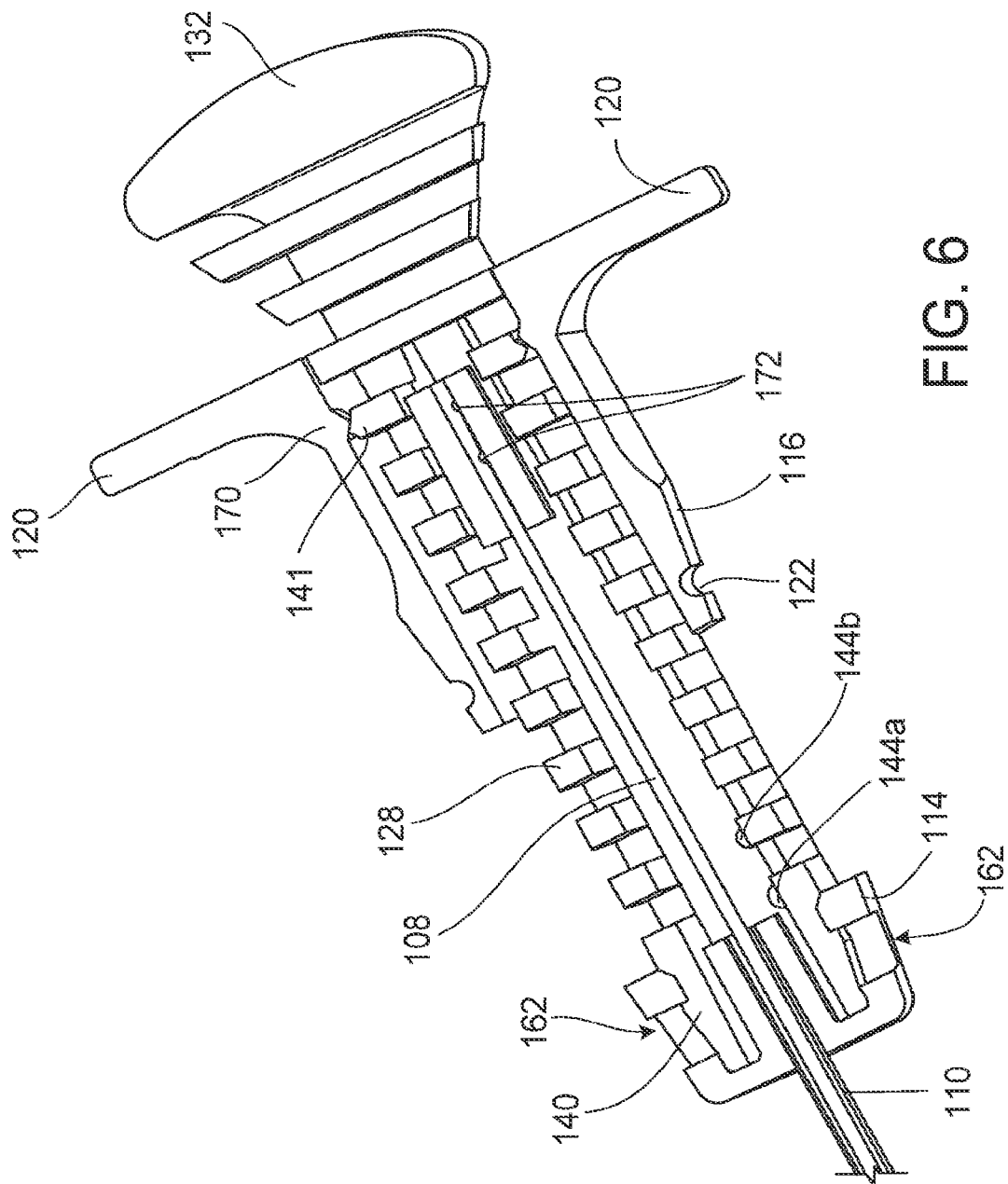
FIG. 6 is a cutaway view of the proximal portion of the delivery device of FIG. 1.

FIG. 6 is a cutaway view of the proximal end of the delivery device 100. The trigger 116 is shown pulled back towards the end of the proximal end 133 of the body 134 of the handle 128. This is considered the "fully deployed" position, as described below. When the trigger 116 reaches the fully deployed position the protrusions 170 of the trigger 116 are forced over the protrusions 141 of the handle 128. This may produce an audible snap, allowing the surgeon to easily recognize when the delivery device 100 has reached its fully deployed state.

Figure 7:
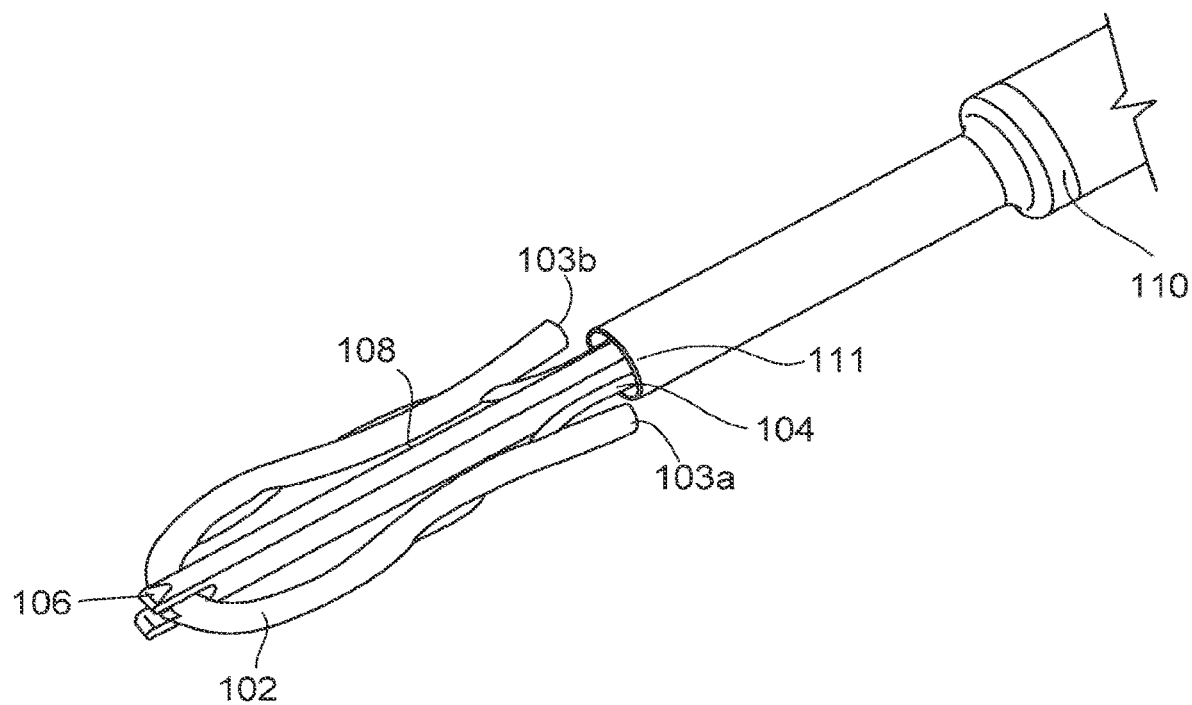
FIGS. 7-9 are perspective views of the distal end of the delivery device of FIG. 1.
Figure 9:
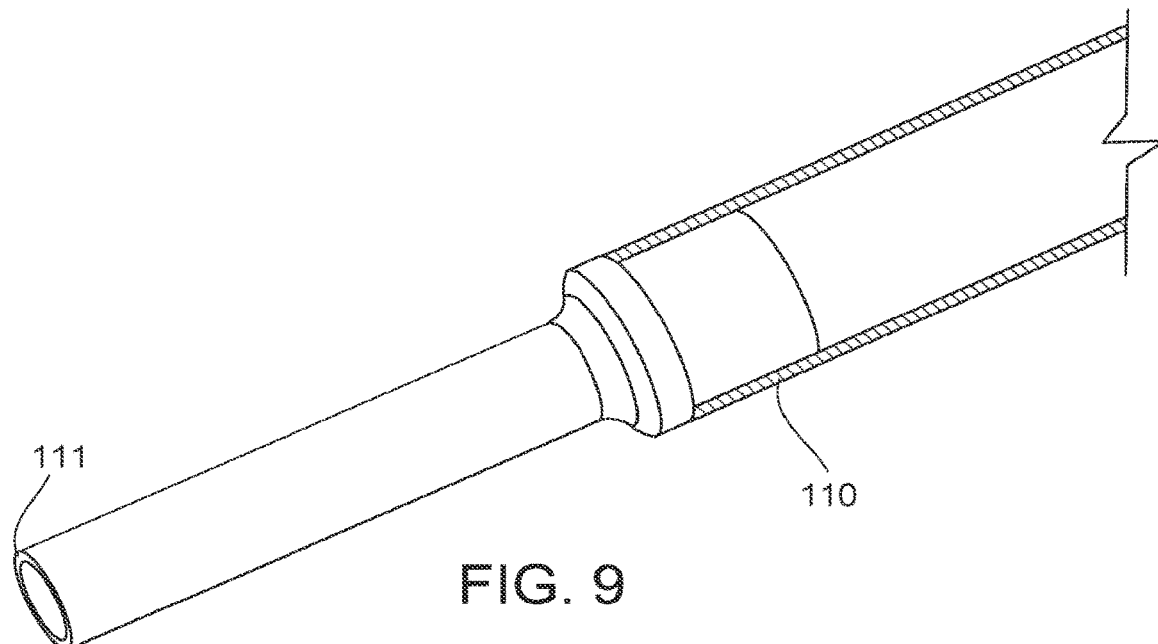
Figure 10:
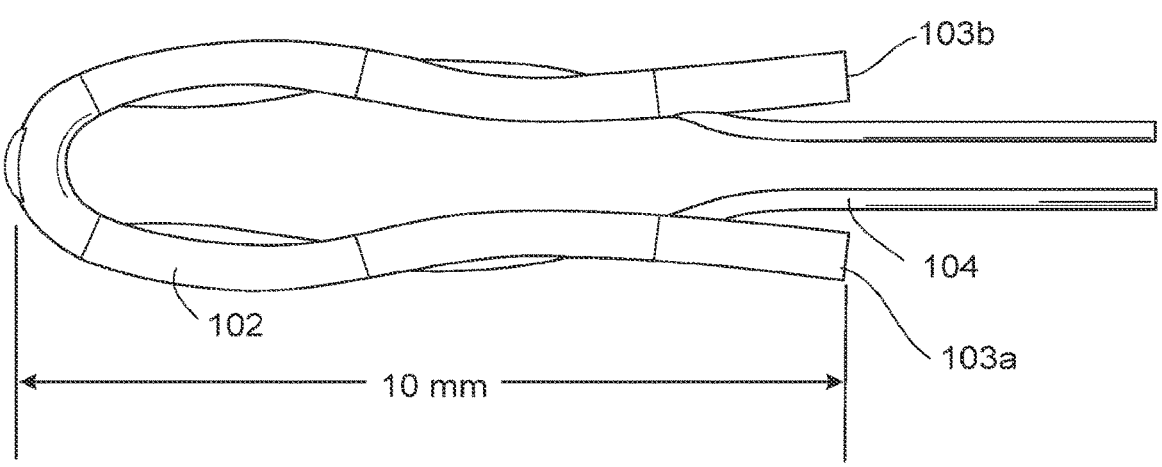
FIG. 10 is a plan view of a flexible fixation member and suture assembly.

FIGS. 7-9 show the distal end of the delivery device 100. Suture 104 is threaded through a flexible fixation member 102 bent in a general u-shape and having two terminal ends 103a, 103b (FIG. 10). The flexible fixation member 102 is formed of a malleable or flexible body. The suture 104 includes two terminal ends (not shown). One of the terminal ends is passed through the flexible fixation member 102 forming multiple curved portions of the suture 104. The suture 104 may slide with respect to the flexible fixation member 102 to form a cluster or bunch 30 including a number of folds as shown in FIG. 12C. The bunch 30 may be used to secure tissue within a surgical site as will be described in more detail below.

Portions of the suture 104 and flexible fixation member 102 are seated in a forked distal end 106 of the elongated inserter 108. The elongated inserter 108 is rectangular in cross-section but could be any types of shapes, including circular, hexagonal, triangular, polygonal, or other suitable shape. The flat sides of the elongated inserter 108 allow the suture to pass through the smaller distal end 111 of the tubular member 110 with the elongated inserter 108 without being pinched or compressed. The elongated inserter 108 transitions from a rectangular profile at the distal end 106 to a circular profile at the proximal end and mates with the tongue 156 of the trigger 116, as illustrated in FIG. 8.

Figure 11A:
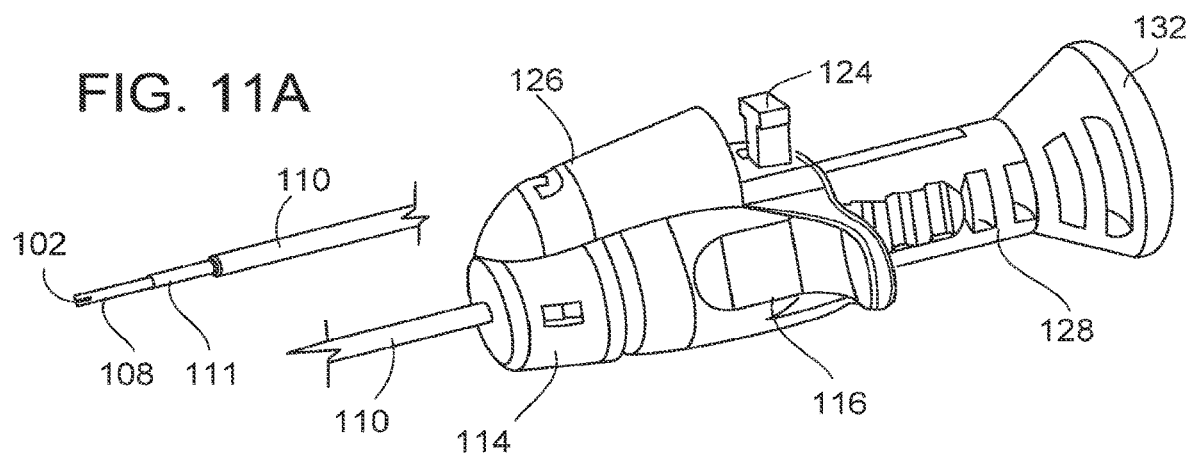
FIGS. 11A-11C illustrate the method of use of the proximal end of a delivery device.
Figure 11B:
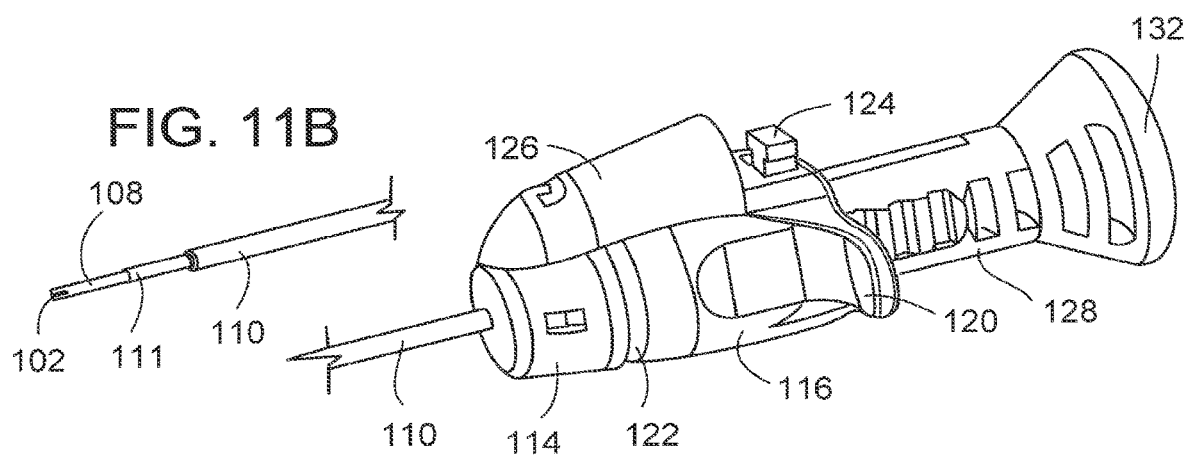
Figure 11C:
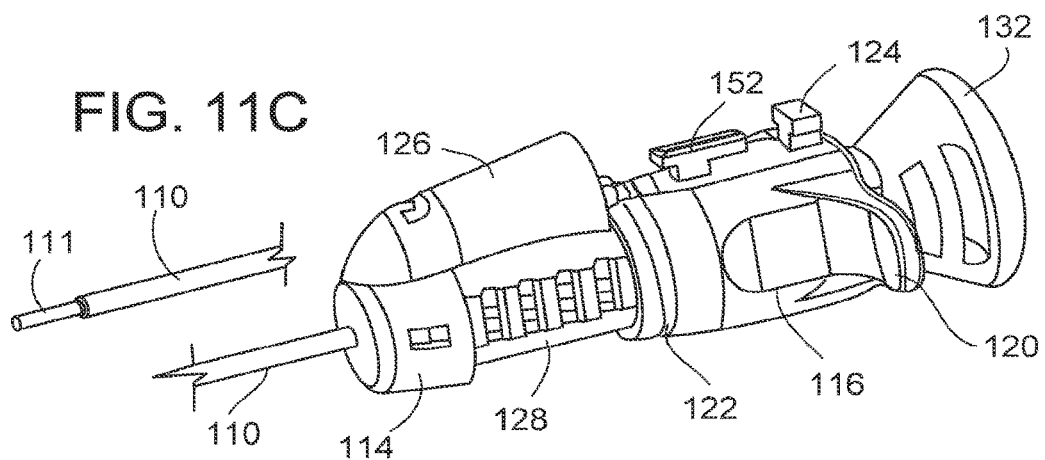
Figure 12A:
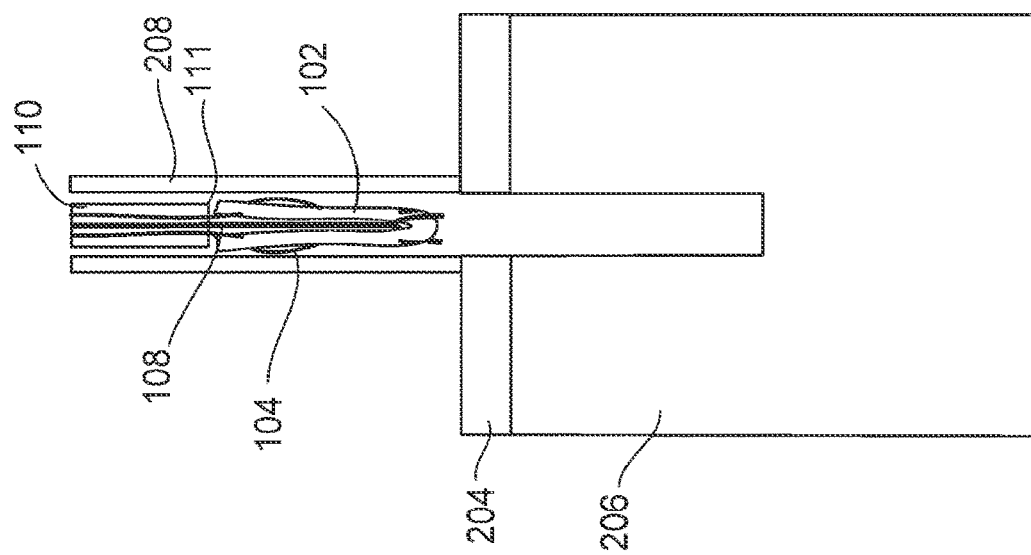
FIGS. 12A-12C illustrate the method of use of the distal end of a delivery device with the flexible fixation member and suture assembly of FIG. 10.
Figure 12B:
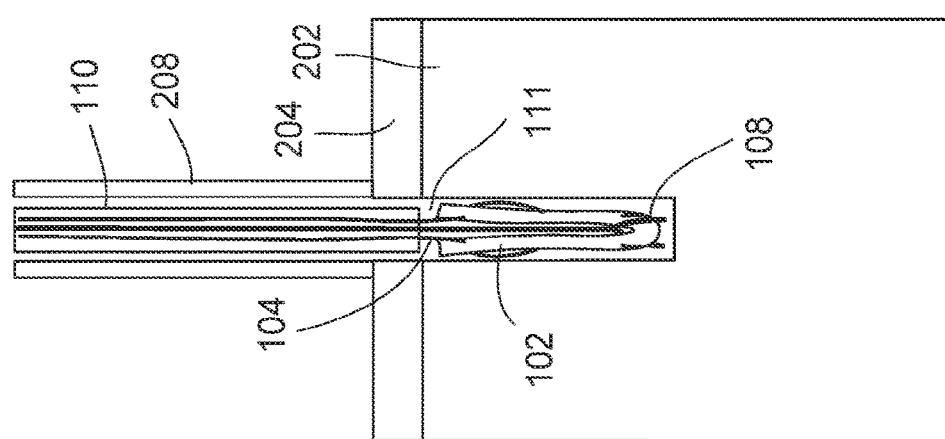
Figure 12C:
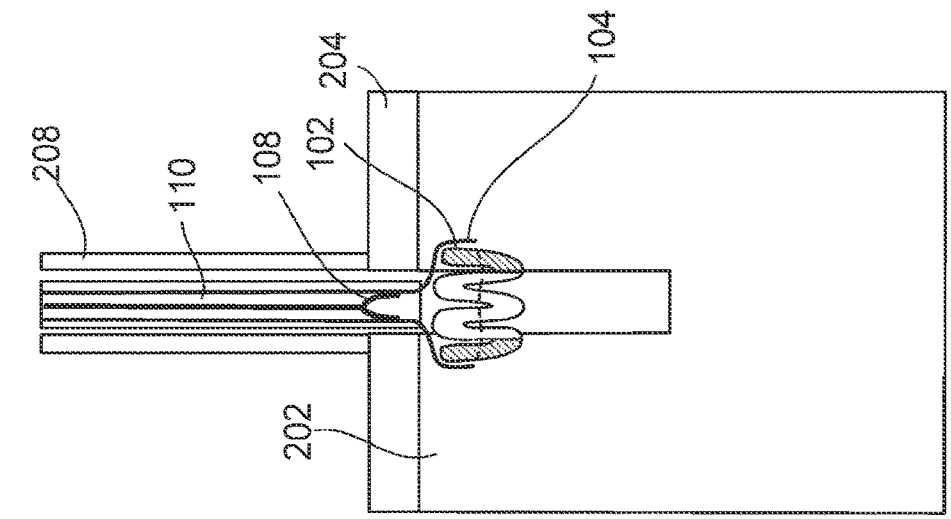

FIGS. 11A-11C and 12A-12C illustrate a method of using the delivery device 100 of FIG. 1 to deploy a flexible fixation member 102 to below a cortical layer 204. FIG. 11A shows a delivery device 100 which is ready for use. The delivery device 100 is loaded with a flexible fixation member 102 and suture 104 assembly (FIG. 10). The suture 104 is routed through the tubular member 110 and through the delivery device 100 as described above, and then secured in retention member 152. The cover 126 hides the suture 104 that is secured in the retention member 152 to prevent premature uncleating of the suture 104, for example, by a user pulling the suture 104 loose from the retention member 152. Referring to FIGS. 12A-12C, a hole 202 is drilled through the cortical layer 204 and into the cancellous layer 206 of bone using a drill guide 208. The distal end of the delivery device 100 is inserted into the drill guide (FIG. 12A). As the distal end of the delivery device 100 is advanced through the drill guide 208, the forked distal end 106 of the elongated inserter 108 moves the flexible fixation member 102 and suture 104 assembly past the cortical layer of bone 204 and into the cancellous layer 206 until the distal end 111 of the tubular member 110 is generally aligned with or past the bottom of the cortical layer 204, as shown in FIG. 12B. The button 124 is then depressed to allow the trigger 116 to be pulled towards the proximal end 132 of the handle 128 (FIG. 11B), pulling the elongated inserter 108 and the suture 104 back. As the trigger 116 is moved toward the proximal end 132 of the handle 128, the retention member 152 and the suture 104 secured therein become accessible.

As the trigger 116 is retracted, the elongated inserter 108 is drawn up into the tubular member 110, slack in the suture 104 is taken up, and the suture 104 is tensioned. The flexible fixation member 102 is larger than the distal tip 111 of the tubular member 110. As the elongated inserter 108 and the suture 104 are drawn back, the flexible fixation member 102 begins to bunch against the distal edge 111 of the tubular member 110. When the trigger 116 is fully retracted, the flexible fixation member 102 is bunched such that it will not pull out of the hole 202 drilled in the bone. The suture 104 can then be uncleated from the retention member 152.

The level of tension of the suture 104 may also be adjusted, prior to retraction of the trigger 116, to facilitate retention of the flexible fixation member 102 in the bone. In general, the flexible fixation member 102 exerts a hoop stress upon the bone surrounding the hole 202, displacing the adjacent bone and retaining the flexible fixation member 102 in place. As the density of the bone increases, however, the degree to which the flexible fixation member 102 displaces adjacent bone may decrease for a given hoop stress. In turn, the degree to which the flexible fixation member 102 is secured within the bone may decrease. By increasing the level of tension within the suture 104 prior to retraction of the trigger 116 (e.g., by suture routing as illustrated above in FIGS. 4F-4H), the hoop stress exerted by the flexible fixation member 102 may be increased. Accordingly, when employing the surgical device 100 to deposit a flexible fixation member 102 in relatively dense bone, it may be desirable to increase the level of tension within the suture 104 prior to retraction of the trigger 116.

Figure 13A:
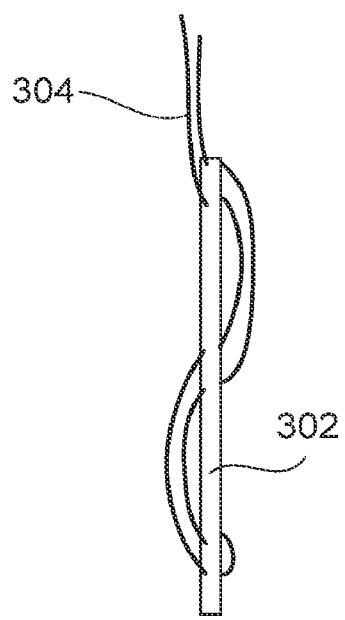
FIG. 13A is a plan view of a flexible fixation member and suture assembly.
Figure 13E:
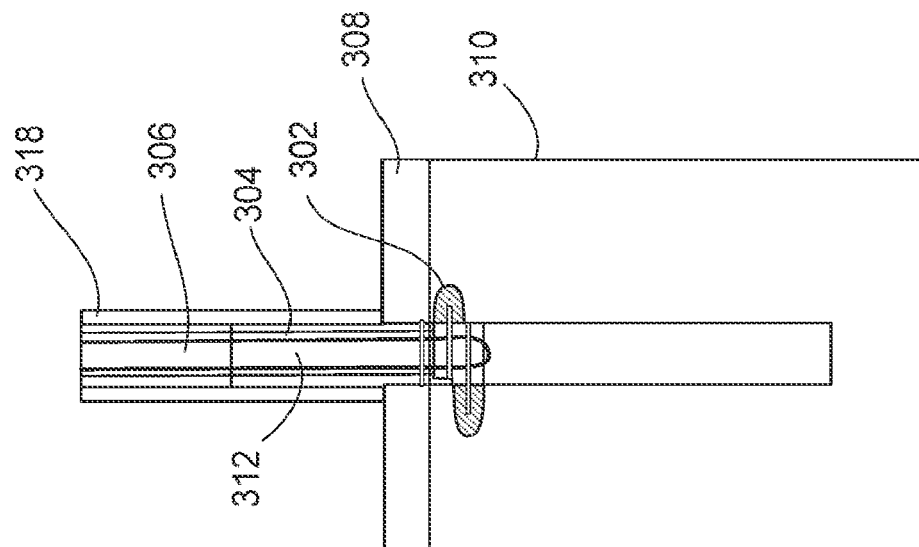
Figure 13D:
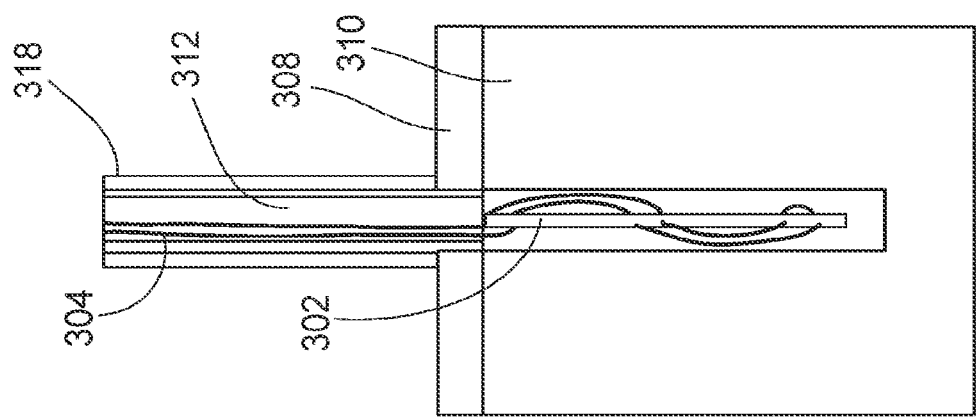

FIG. 13A is an alternative implementation of weaving the suture 304 through the flexible fixation member 302. In this implementation, the flexible fixation member 302 is not bent into au-shape, but is substantially straight while both ends of the suture 304 are inserted in and out of the flexible fixation member 302. This implementation also includes an outer tubular member 306 which is inserted through the cortical layer 308 and into the cancellous layer 310 with the flexible fixation member 302 and suture 304 assembly. This outer tubular member 306 provides additional protection for the flexible fixation member 302 and suture 304, and prevents any pinching or other damage to the flexible fixation member 302 or suture 304 during insertion.

The method of delivery is similar to the method described above. The suture 304 is routed through the tubular member 312 and through the delivery device 100 as described above, and then secured in retention member 152. The cover 126 hides the suture 304 that is secured in the retention member 152 to prevent premature uncleating of the suture 304. A hole 316 is drilled through the cortical layer 308 and into the cancellous layer 310 of bone using a drill guide 318. The distal end of the delivery device 100 is inserted into the drill guide 318 (FIG. 13B). The distal end of the delivery device 100 is advanced through the drill guide 318 until the outer tubular member 306 is past the cortical layer of bone 308 and into the cancellous layer 310 and the distal edge 314 of the tubular member 312 is generally aligned with or past the bottom of the cortical layer 308, as shown in FIG. 13C. The button 124 is then depressed to allow the trigger 116 to be pulled towards the proximal end 132 of the handle 128, as shown in FIG. 11B, pulling the outer tubular member 306 and the suture 304 back. As the trigger 116 is moved toward the proximal end 132 of the handle 128, the retention member 152 and the suture 304 secured therein become accessible. The flexible fixation member 302 is larger than the distal tip 314 of the tubular member 312. As the outer tubular member 306 and the suture 304 are drawn back, the flexible fixation member 302 begins to bunch against the distal edge 314 of the tubular member 312. When the trigger 116 is fully retracted, the flexible fixation member 302 is bunched such that it will not pull out of the hole 316 drilled in the bone. The suture can then be uncleated from the retention member 152.

FIGS. 14A-14D show another implementation of the flexible fixation member 402 and suture 404. In this implementation, the flexible fixation member 402 is straight while one end 405a of the suture 404 is inserted in and out of the flexible fixation member 402 and one end 405b of the suture 404 runs parallel to the straight fixation member 402.

Figure 14B:
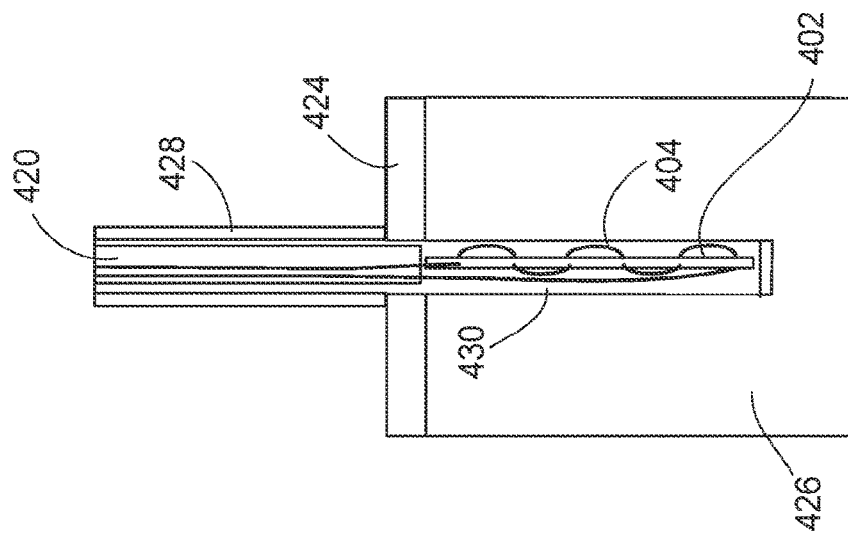
Figure 14A:
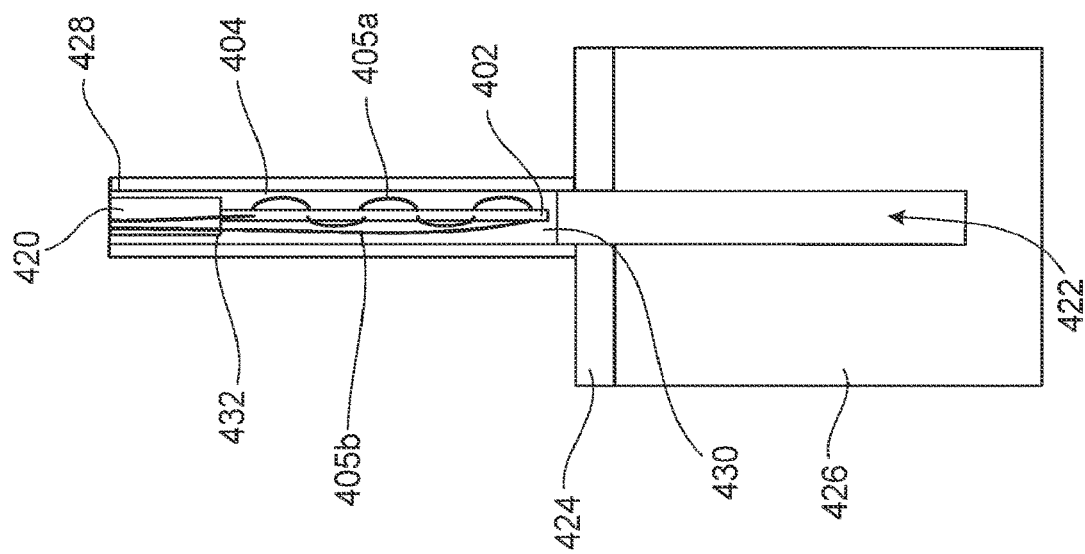

The method of delivery is the same method as described above with respect to FIGS. 13B-13E. The suture 404 is routed through a tubular member 420, through the delivery device 100, and secured in retention member 152. The cover 126 hides the suture 404 that is secured in the retention member 152. A hole 422 is drilled through the cortical layer 424 and into the cancellous layer 426 of bone using a drill guide 428. The distal end of the delivery device 100 is inserted into the drill guide (FIG. 14A). The distal end of the delivery device 100 is advanced through the drill guide 428 until the outer tubular member 430 is past the cortical layer of bone 424 and into the cancellous layer 426 and the distal edge 432 of the tubular member 420 is aligned with or past the bottom of the cortical layer 424, as shown in FIG. 14B. The button 124 is then depressed to allow the trigger 116 to be pulled towards the proximal end 132 of the handle 128, as shown in FIG. 11B, pulling the outer tubular member 430 and the suture 404 back. The flexible fixation member 402 is larger than the distal tip 432 of the tubular member 420. When the trigger 116 is fully retracted, the flexible fixation member 402 is bunched such that it will not pull out of the hole 422 drilled in the bone. The suture 404 can then be uncleated from the retention member 152.

Figure 15A:
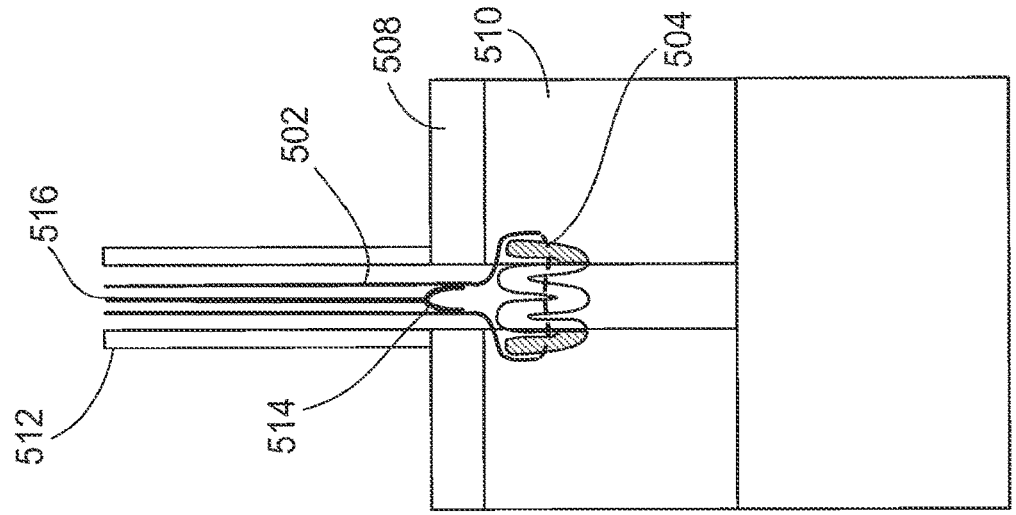
FIGS. 15A-15C illustrate the method of use of the distal end of a delivery device with another flexible fixation member and suture assembly
Figure 15B:
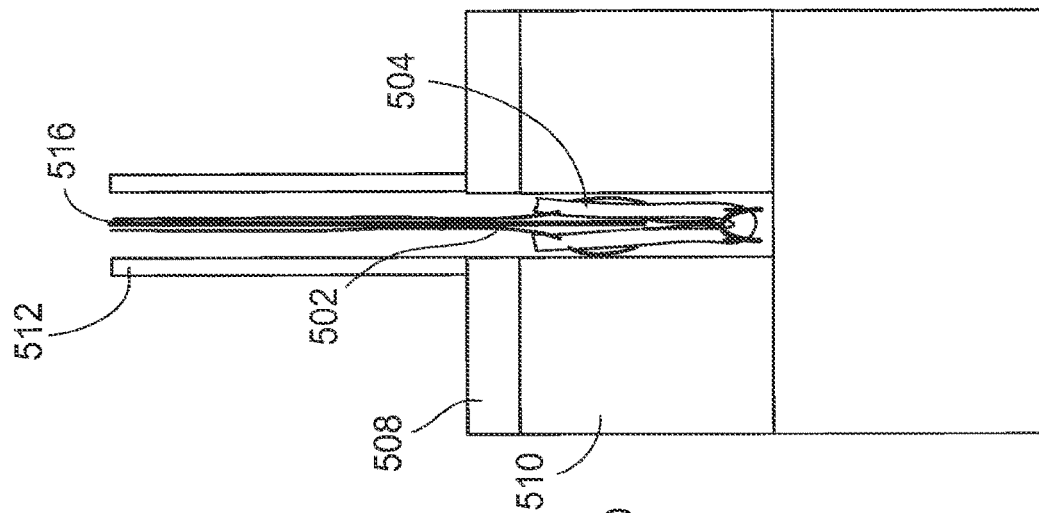
Figure 15C:
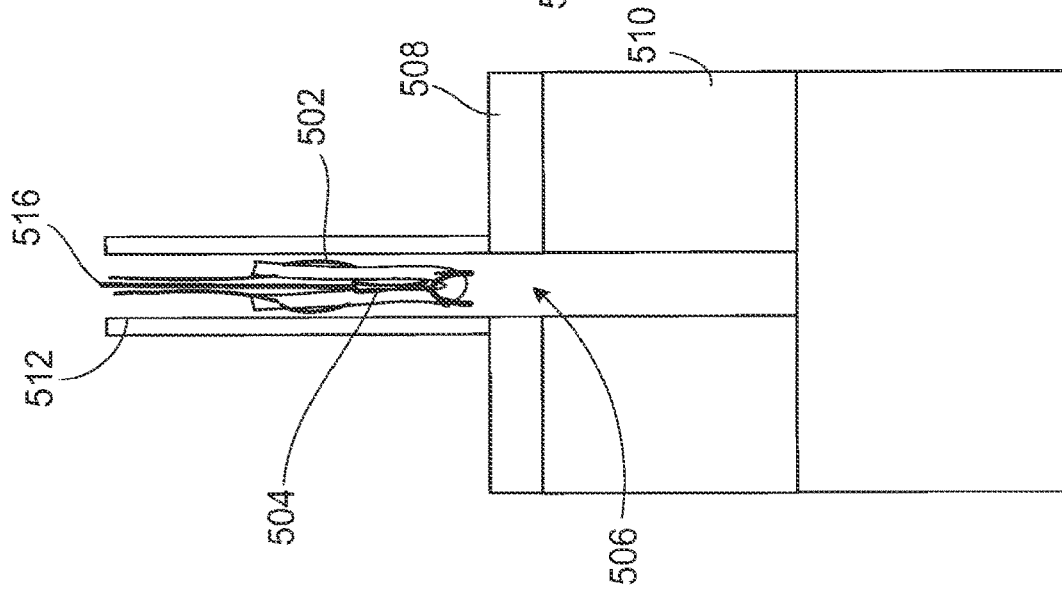
Figure 16A:
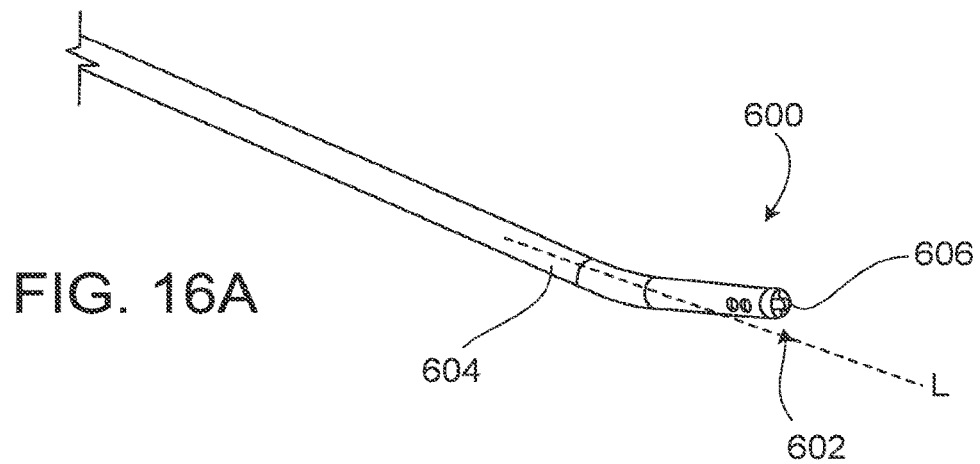
FIGS. 16A-16F are perspective views of an angled guide.
Figure 16B:
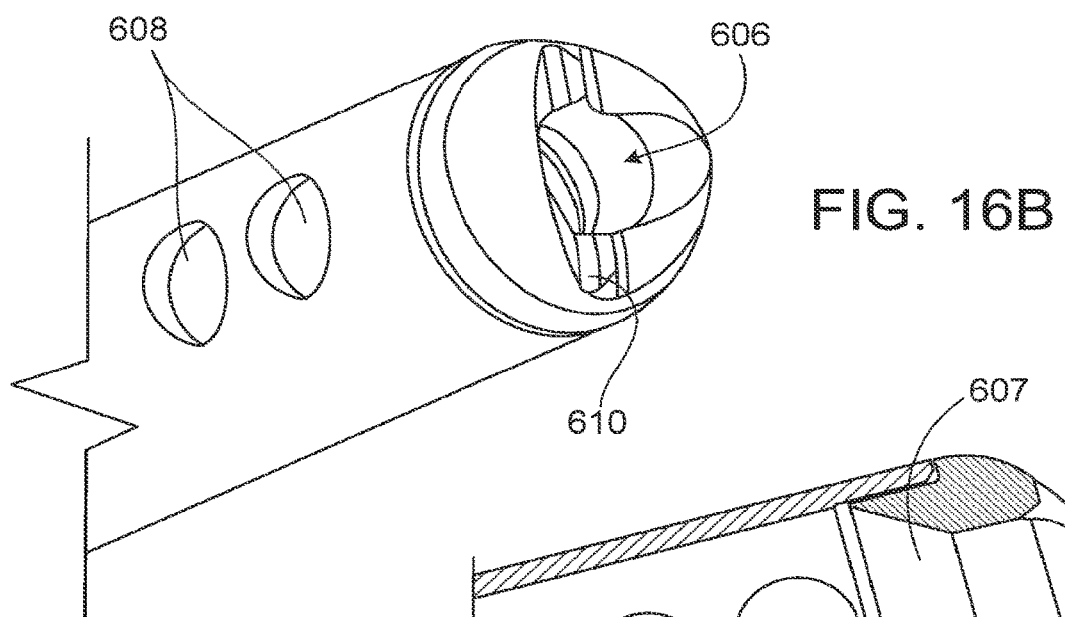
Figure 16C:
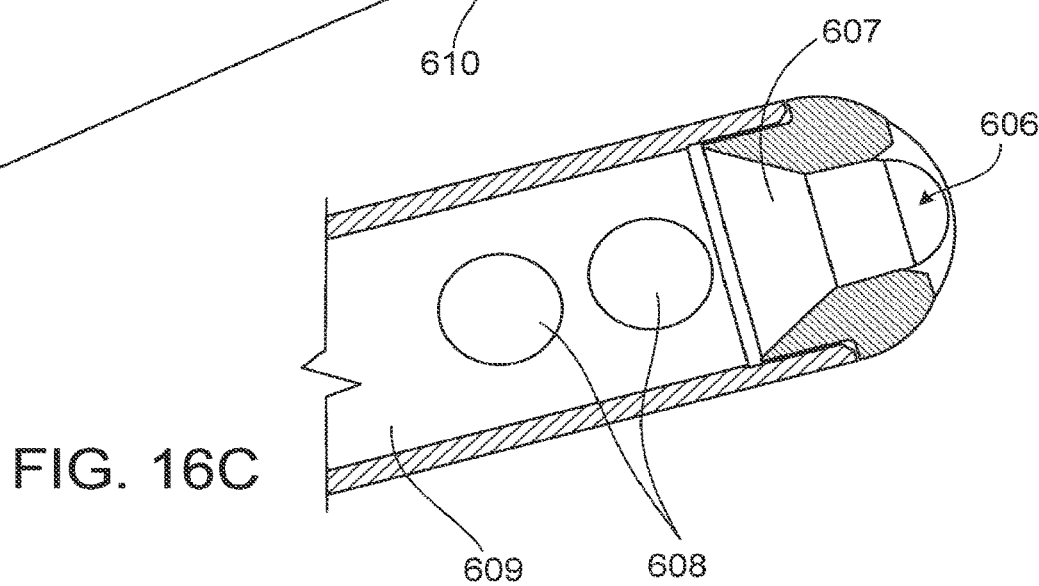
Figure 16D:
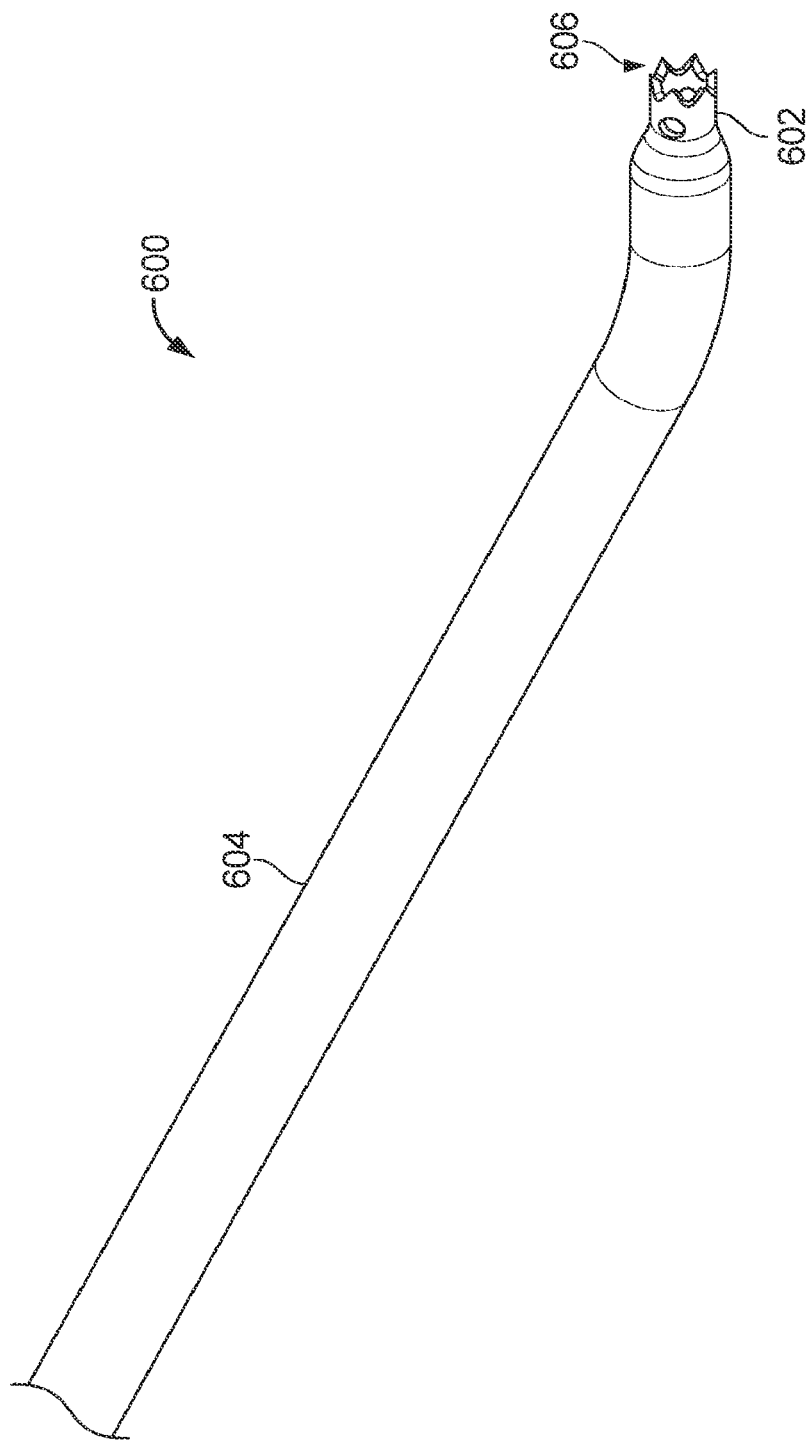
Figure 16E:
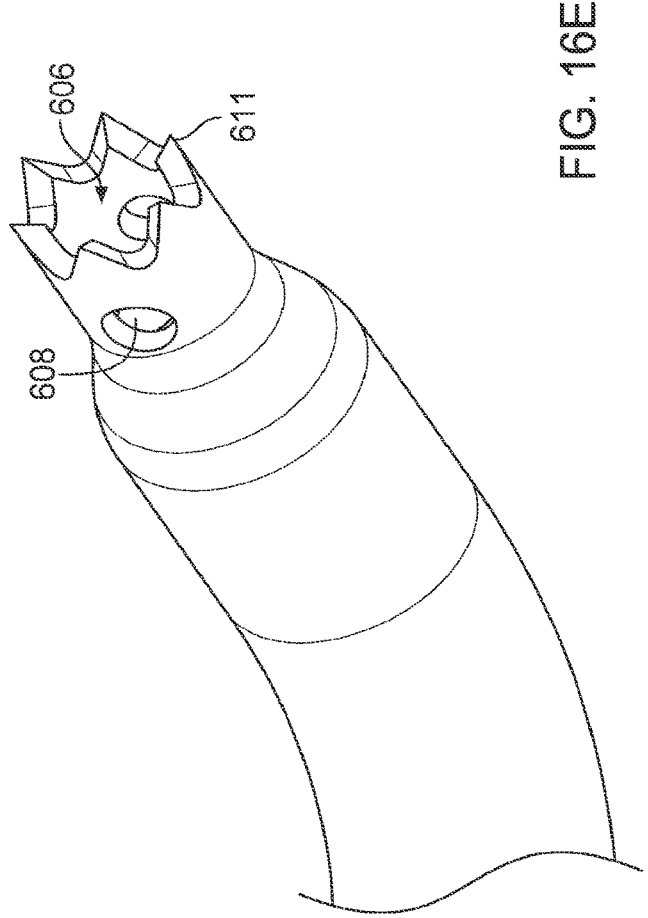
Figure 16F:
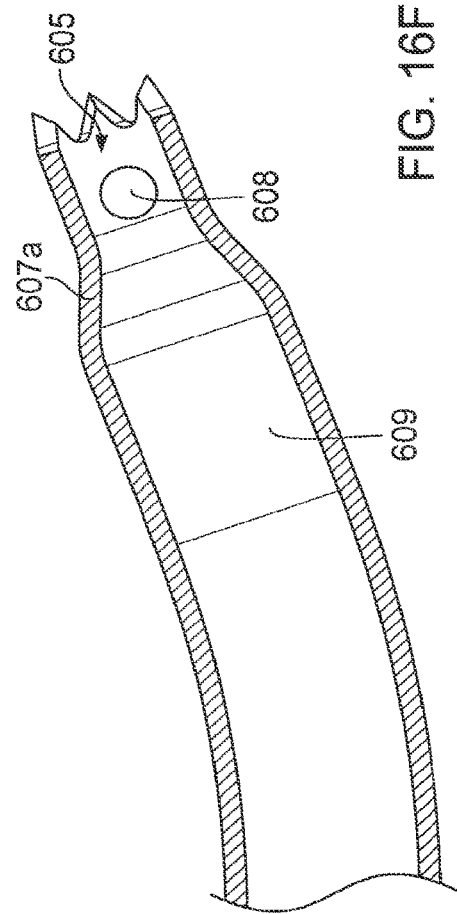
Figure 17C:
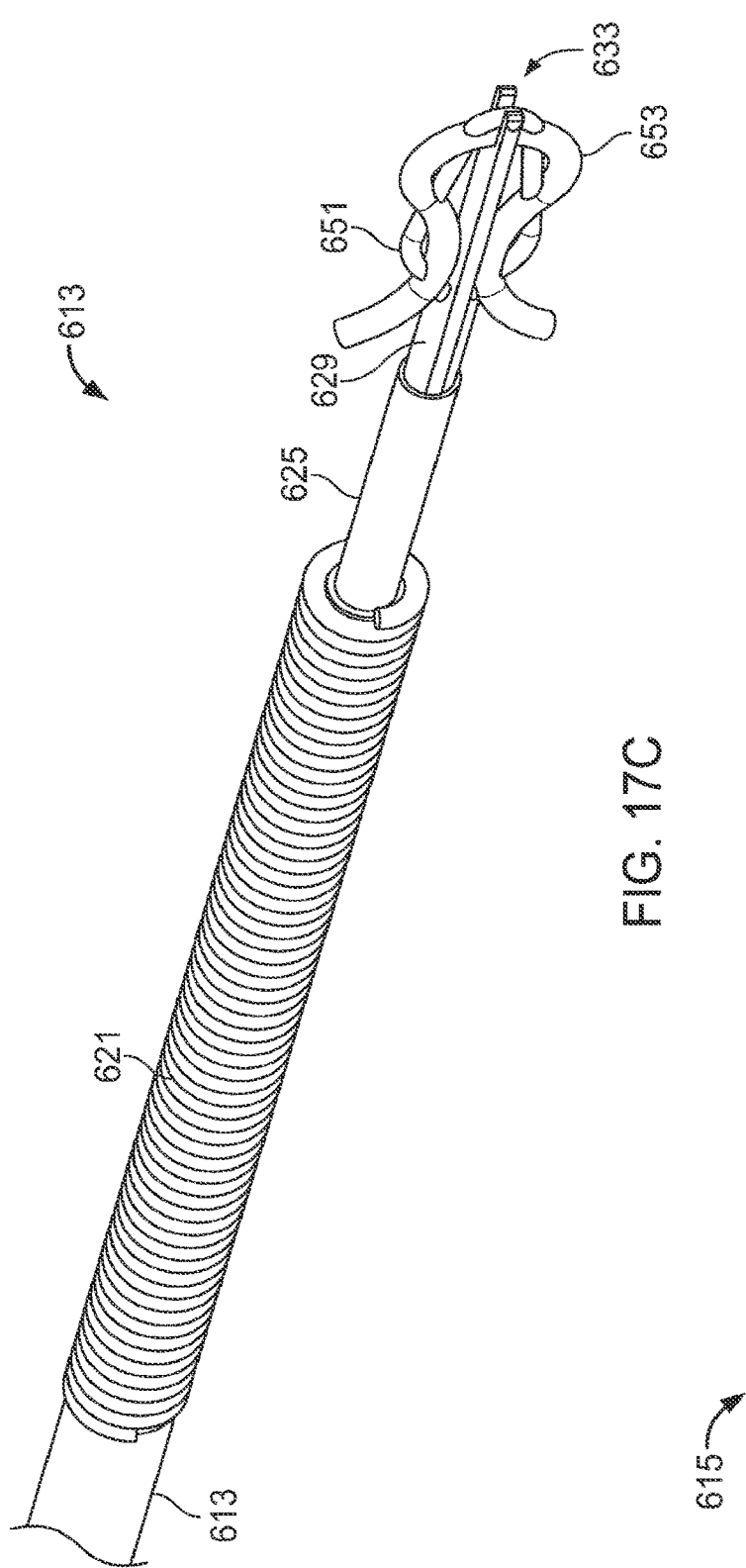
Figure 17D:
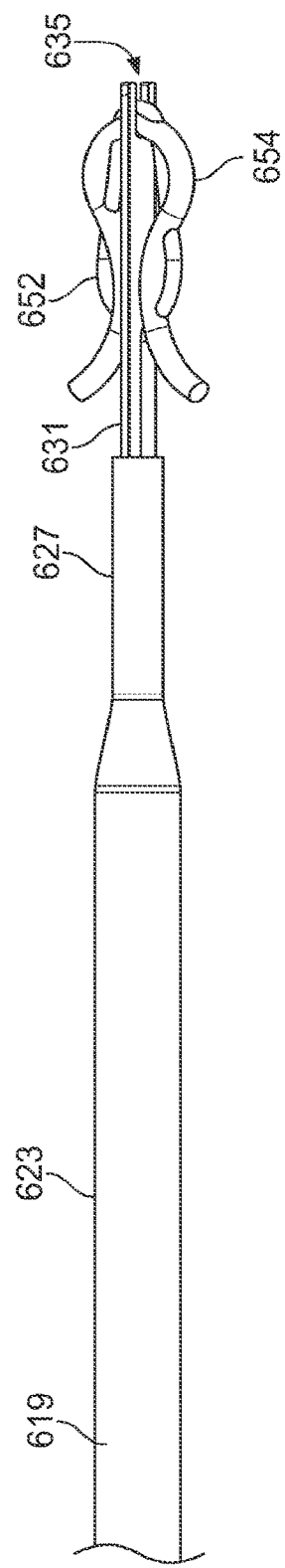
Figure 17E:
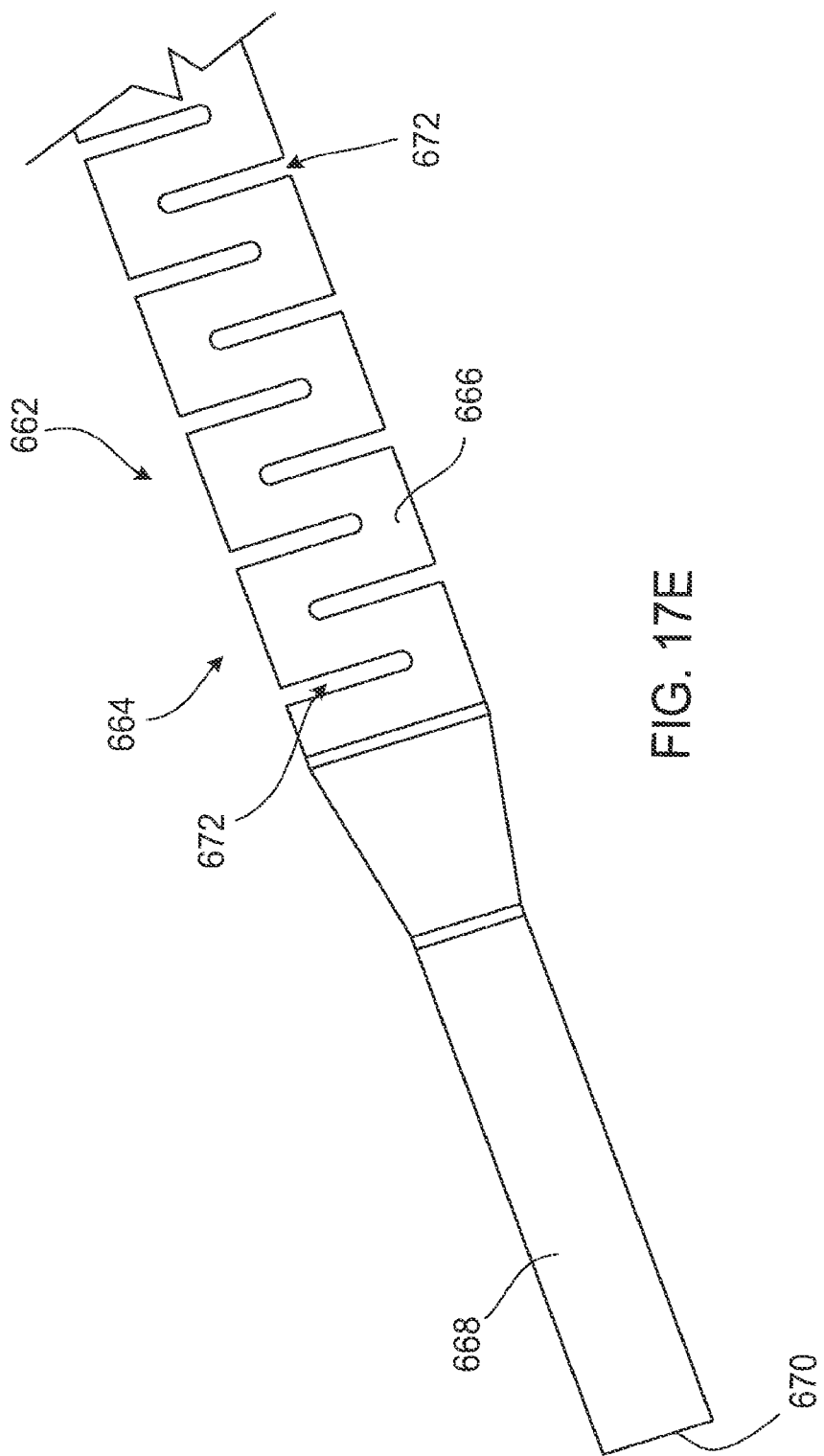

FIGS. 15A-15C show another implementation of the delivery device. In this implementation, the tubular member has been omitted. The method is similar to the method described above with respect to FIGS. 11A-12C. The delivery device 100 is loaded with a flexible fixation member 502 and suture 504 assembly (FIG. 10). The suture 504 is routed through the delivery device 100 as described above, and then secured in retention member 152. The cover 126 hides the suture 504 that is secured in the retention member 152. A hole 506 is drilled in through the cortical layer 508 and into the cancellous layer 510 of bone using a drill guide 512. The distal end of the delivery device 100 is advanced through the drill guide 512 until the forked distal end 514 of the elongated inserter 516 pushes the flexible fixation member 502 and suture 504 assembly past the cortical layer of bone 508 and into the cancellous layer 510, as shown in FIG. 15B. The button 124 is then depressed to allow the trigger 116 to be pulled towards the proximal end 132 of the handle 128 (FIG. 11B), pulling the elongated inserter 516 and the suture 504 back. As the elongated inserter 516 and the suture 504 are drawn back, the flexible fixation member 502 begins to bunch against the cortical layer 508 of bone. When the trigger 116 is fully retracted, the flexible fixation member 502 is bunched such that it will not pull out of the hole 506 drilled in the bone. The suture 504 can then be uncleated from the retention member 152.

Figure 20A:
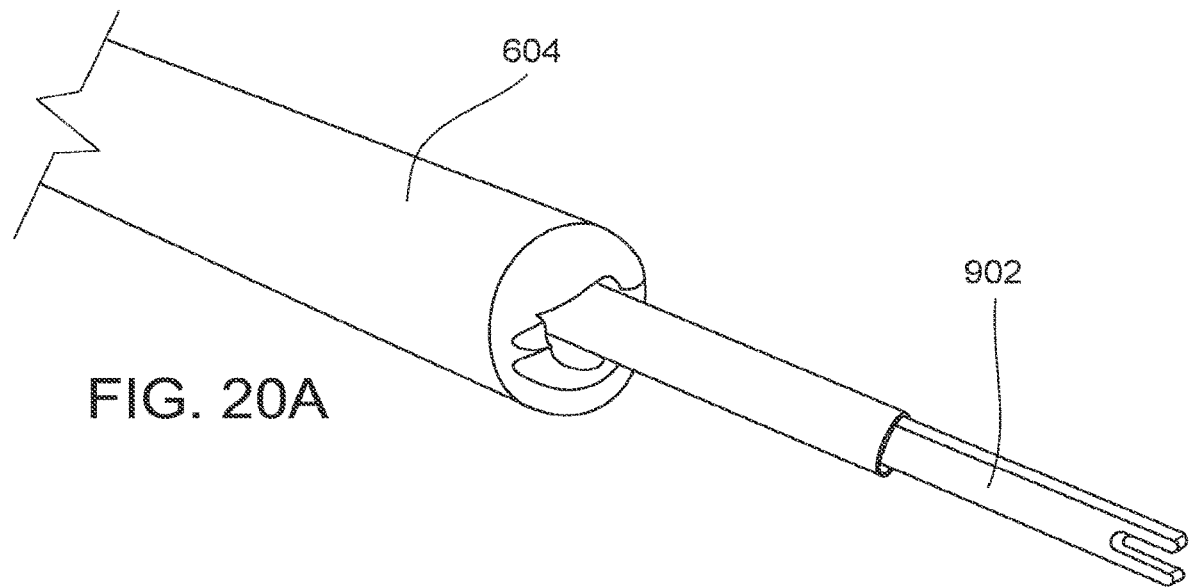
FIG. 20A is a perspective view of the distal end of an angled guide and flexible inserter.
Figure 20B:
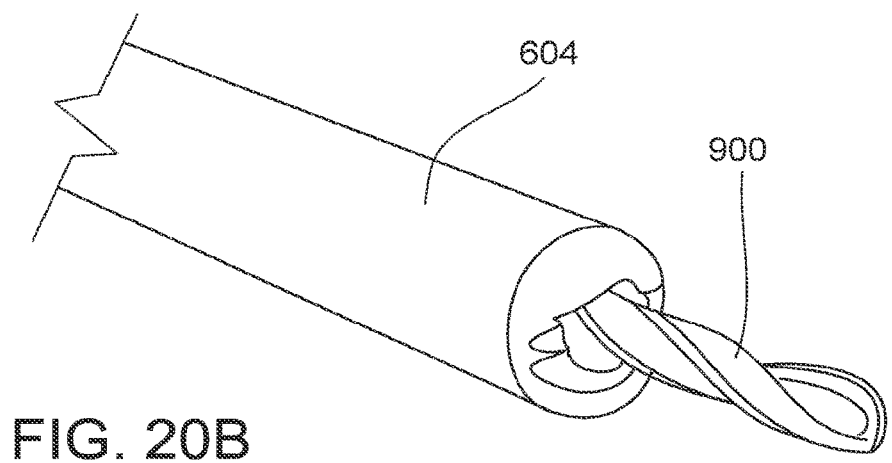
FIG. 20B is a perspective view of the distal end of an angled guide and flexible drill.
Figure 20C:
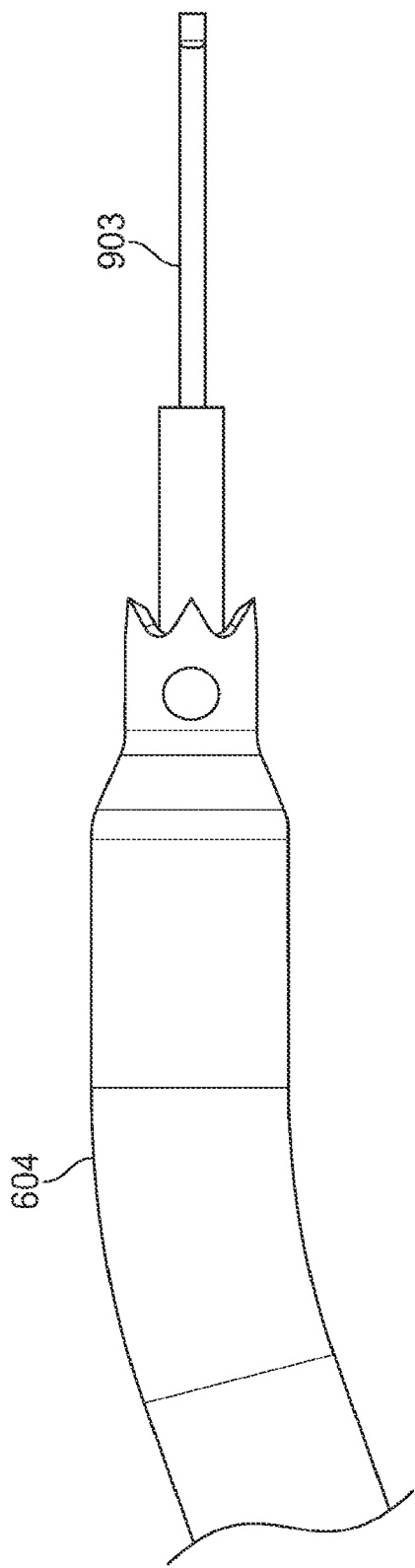
FIG. 20C is a perspective view the distal end of an angled swaged guide and flexible inserter.
Figure 20D:
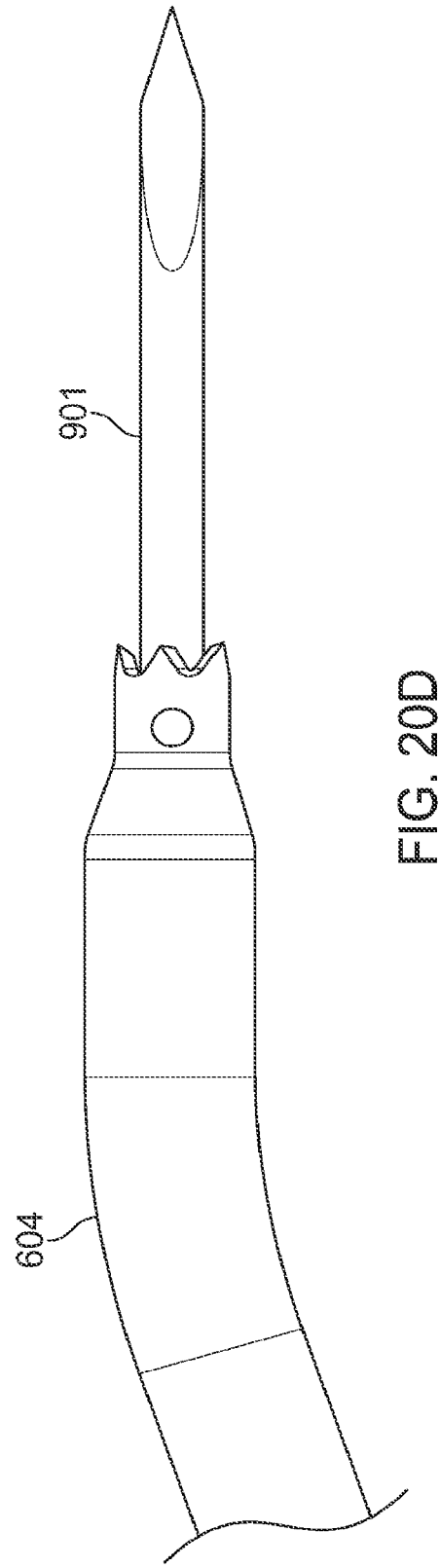
FIG. 20D is a perspective view of the distal end of an angled guide and flexible drill.

FIGS. 16A-16F show another implementation of the delivery device 600. A guide 604 includes a distal end portion 602 that is angled relative to a longitudinal axis L of the guide 604, which allows the surgeon to achieve the ideal insertion angle of, for example, a flexible drill, such as the Flexible Twist Drill for 2.3 Osteoraptor™ Curved Guide, available from Smith & Nephew, Inc. of Andover MA, and/or a flexible suture inserter at a quicker rate, thereby reducing the potential of damage to cartilage and other tissue within the joint area. The distal end portion 602 of the guide 604 defines an opening 606 which is narrowed down via a cut or bushing 607 or swaged structure 607a placed in the distal end portion 602 (FIG. 16C, 16F) relative to the remainder of the cannula 609 of the guide 604. This narrowed portion aids in stabilizing and centering a flexible drill bit 900, 901 or a flexible inserter 902, 903 as it exits the guide 604 through the opening 606, 605, as shown in FIGS. 20A, 20B, and 20C. The distal end portion 602 also includes one or more holes 608. The holes 608 are used during surgery to view the tissue anchor and, specifically the orientation of the tissue anchor, prior to inserting the anchor into tissue, such as bone. The holes 608 may also be used to vent bone and other debris that may become located within the distal end portion 602 of the guide 604 during surgery. The distal end portion 602 of the guide 604 also includes a serrated edge 610, 611 for facilitating maintenance of the guide 604 on the bone during surgery, thereby substantially reducing slippage of the guide 604 off of the bone. Rather than a serrated edge 610, 611, the edge 610, 611 may have other features known to one of skill that would help in maintaining the guide 604 on the bone and reduce slippage. The curved guide 604 is further described in WO 2012/048050, which is incorporated herein by reference in its entirety.

FIGS. 17A through 17E illustrate exemplary implementations of a flexible elongated inserter 612, 614, 613, 615, 662, respectively, that may be used in conjunction with the guide 604 for delivering anchors, such as the suture anchors described above, into tissue. The flexible elongated inserters 612, 614, 613, 615, 662 each include an outer tubular member 616, 618, 617, 619, 664, which includes at least a flexible portion 620, 622, 621, 623, 666 and a rigid, thinned portion 624, 626, 625, 627, 668 extending to a distal end 628, 630, 629, 631, 670 of the respective inserters 612, 614, 613, 615, 662. The flexible portion 620, 622, 621, 623, 666 permits the inserter 612, 614, 613, 615, 662 to substantially conform to the shape of the guide 604 when the inserter 612, 614, 613, 615, 662 is moved through the cannula 607 or 607a of the guide 604. The flexible portion 620, 622, 621, 623, 666 may be made of a flexible material, such as, for example, nitinol or flexible plastics, or may be made from a coil cut tube (FIG. 17A), or a collection of engaging elements forming a puzzle cut tube (FIG. 17B), or a spring (FIG. 17C), or biocompatible flexible materials tube such as PEEK (FIG. 17E), or with alternating slits (N degree alternation, N=90 or 180 or other angles) (FIG. 17E), or other designs known in the art. The distal end 628, 630,629, 631 of each of the inserters 612, 614, 613, 615 includes a pronged-end 632, 634, 633, 635, which receives a portion of a suture 650 (FIG. 17B), 651 (FIG. 17C), 652 (FIG. 17E) and a suture anchor 653 (FIG. 17C), 654 (FIG. 17D) as described above. The distal end 670 of inserter 662 may also include a pronged-end (not shown) which receives a portion of a suture and a suture anchor as described above.

Figure 18A:
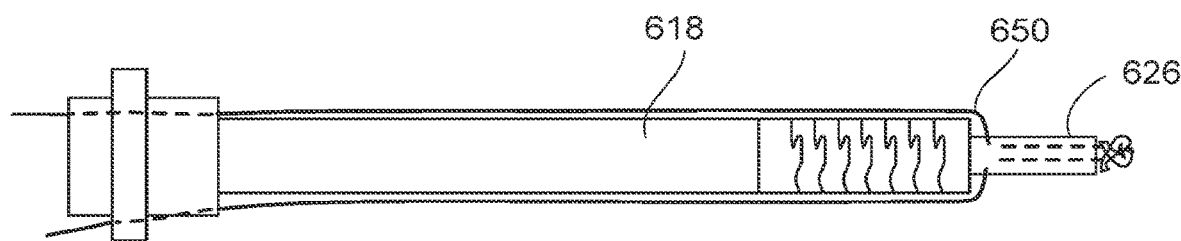
FIG. 18A is a plan view of a flexible delivery device with a suture routed externally.
Figure 18B:
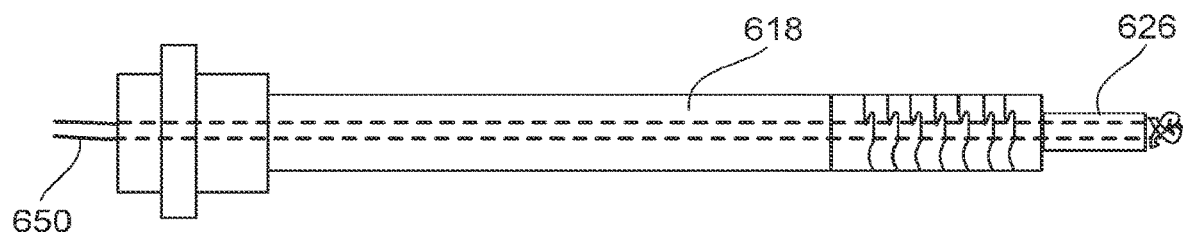
FIG. 18B is a plan view of a flexible delivery device with a suture routed internally.

Referring to FIG. 18A, the repair suture 650 may be routed through a portion of the rigid portion 626 of the outer tubular member 618 for a certain distance, and then exit the outer tubular member 618 at a point along the rigid portion 626 or flexible portion 620. Upon exit from the outer tubular member 618, the suture 650 is then routed proximally along the outside of the outer tubular member 618 and between the guide 604. This helps protect the suture from damage during use. In the alternative, as shown in FIG. 18B, the repair suture 650 may be routed proximally within the outer tubular member 618. The same suture routing method is applicable to all the inserter options shown in FIG. 17.

The method of use of delivery device 600 is similar to the method described above with respect to FIGS. 11A-12C. The curved guide 604 is placed against the cortical layer of tissue. The flexible drill 900 is delivered through the curved guide 604 and used to form a hole in the bone below the cortical layer. Once the hole is formed, the flexible drill 900 is removed from the guide 604 and the flexible inserter 902 is inserted through the guide 604. As described above, the repair suture and suture anchor are preloaded onto the forked end of the flexible inserter 902. The flexible inserter 902 is advanced through the guide 604 past the cortical layer of bone and into the cancellous layer. The flexible elongated inserter 902 is then retracted and the suture anchor is bunched such that it will not pull out of the hole drilled in the bone, as described with respect to FIGS. 11A-12C.

Figure 19A:
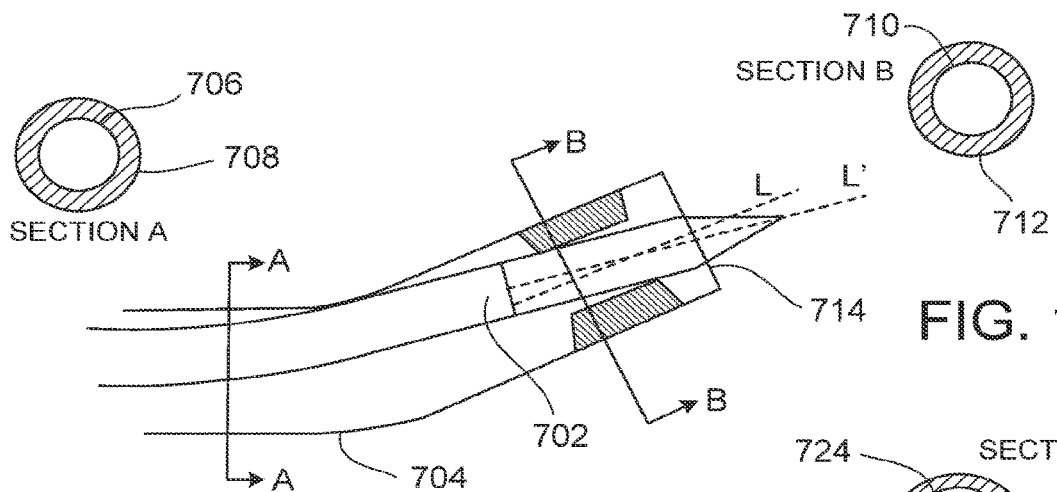
FIGS. 19A-19C are plan views of angled guides and a flexible drill or inserter.
Figure 19B:
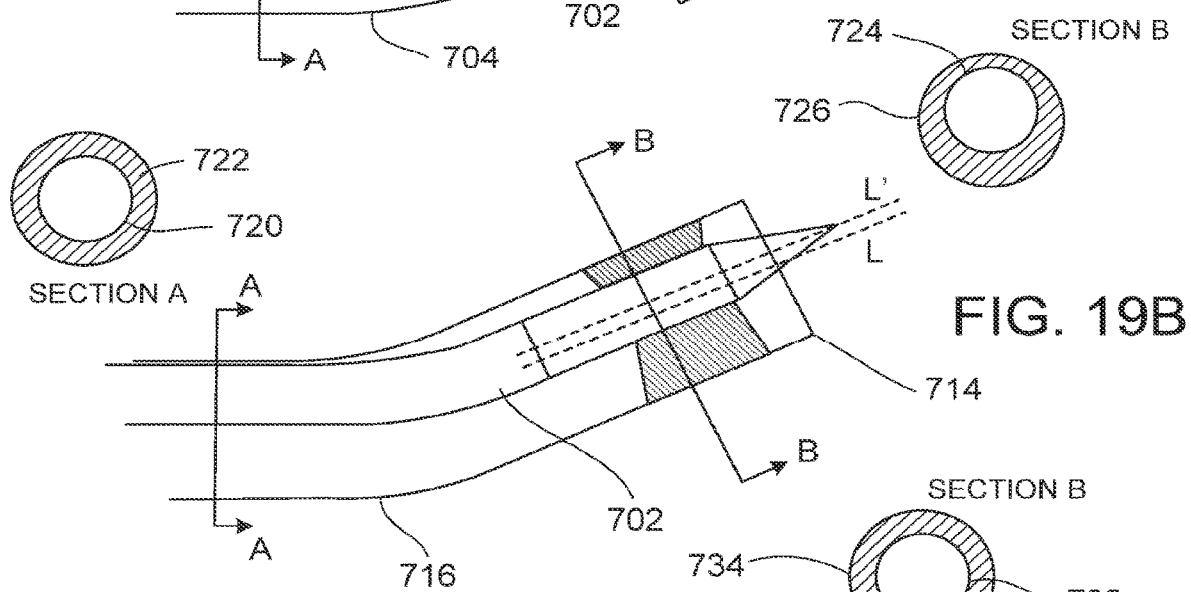
Figure 19C:
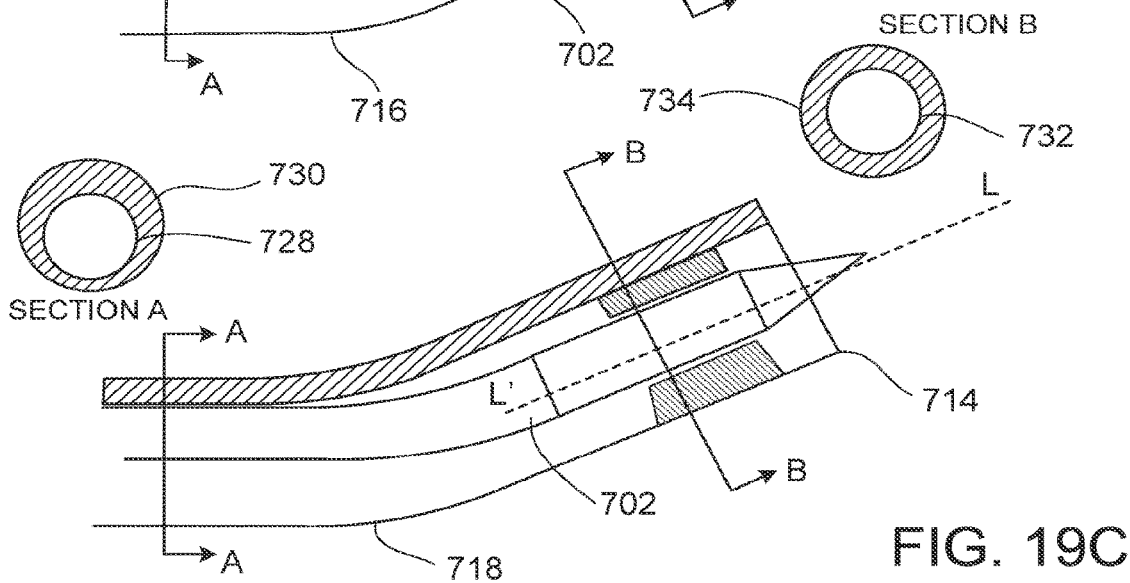

As discussed above, the distal end portion 602 of the guide 604 defines an opening 606 which narrows down via a cut or bushing 607 placed in the distal end portion 602 (FIG. 16C) relative to the remainder of the cannula 609 of the guide 604. This narrowed portion aids in stabilizing and centering a flexible drill bit 900 or a flexible inserter 902 as it exits the guide 604. FIGS. 19A-19C illustrate additional implementations for assisting in the centering of the drill bit or inserter trajectory from the guide 604. As shown in FIG. 19A, a flexible drill or inserter 702 is inserted within a curved guide 704. The curved guide 704 has a first inner diameter (ID) 706, which is concentric with a first outer diameter (OD) 708 as taken along line A-A of FIG. 19A. The guide 704 has a second ID 710, which is concentric with a second OD 712 as taken along line B-B of FIG. 19A. In this implementation, the longitudinal axis L' of the drill or inserter 702 may be angularly offset from the longitudinal axis L of the distal end 714 of the curved guide 704 because the drill or inserter 702 tends to remain straight.

FIGS. 19B and 19C show implementations of angled guides 716, 718 that aid in aligning the longitudinal axes L, L' of the flexible drill or inserter 702 and the guide 716, 718. FIG. 19B shows a guide 716 with a first ID 720, which is concentric with a first OD 722 as taken along line A-A of FIG. 19B, and a second ID 724, which is eccentric with respect to a second OD 726 taken along line B-B of FIG. 19B. The second ID 724 is offset toward the inside of the guide 716. The offset second ID 724 brings the longitudinal axis L' of the distal end of the drill or inserter 702 into substantial angular alignment with the longitudinal axis L of the distal end of the guide 716. FIG. 19C shows a guide 718 with a first ID 728, which is eccentric with respect to a first OD 730 as taken along line A-A of FIG. 19C, and a second ID 732, which is concentric with a second OD 734 taken along line B-B of FIG. 19C. The first ID 728 is offset toward the outside of the guide 718. The offset first ID 728 brings the longitudinal axis L' of the distal end of the drill or inserter 702 into alignment with the longitudinal axis L of the distal end of the guide 718. In addition to aligning the longitudinal axes L, L', the offset IDs and ODs may allow the device to support higher loads. For example, when bent, the concave side of the bent drill or inserter 702 supports the compressive or tensional loads. Thus, by thickening the wall of the concave side, more load may be supported.

The embodiments of FIGS. 19A-19C, illustrating additional implementations for assisting in the centering of the drill bit or inserter trajectory from the guide 604, may also be combined with embodiments of the cut/bushing 607 or swaged structure 607a illustrated in FIGS. 16A-16F.

A number of implementations have been described. Nevertheless, it will be understood that various modifications may be made without departing from the spirit and scope of the disclosure. For example, the fixation members and the flexible members may include a growth factor, such as, for example, an angiogenic factor. The fixation members and the flexible members may also be loaded with a bioactive material, a stimulant, or any substance that promotes healing of the tissue. In addition, the handle may include more than one cut out portion to allow the trigger to be secured at different places along the body of the handle. Moreover, the hollow cavity of the cover element may have more than two straight portions, one straight portion, or no straight portions. Elements 146 and 148 have been described as slots, but may be through holes or other shapes.

In addition, although the elongated inserter has been described as having a rectangular profile at its distal end and a circular profile at its proximal end, other profile combinations, as well as constant profiles are contemplated.

Moreover, in addition to the particular materials described, the elements of the delivery device may be made from other suitable materials. For example, the handle may be injection molded and made of polycarbonate. Accordingly, other implementations are within the scope of the following claims.

What is claimed is:

1. A surgical assembly comprising:
an all-suture anchor;
a suture slidably received by the all-suture anchor such that the all-suture anchor can bunch up relative to the suture;
an elongate member including a forked distal end; and
a proximal portion proximal to the elongate member, the proximal portion defining a circular groove;
wherein the all-suture anchor and the suture are received on the forked distal end such that the suture extends proximally along an external surface of the elongate member and through the proximal portion, and wraps around the proximal portion within the circular groove; and
wherein the circular groove is oriented perpendicular to a longitudinal axis of the elongate member.

2. The surgical assembly of claim 1, wherein the all-suture anchor comprises a flexible body formed by two legs and a U-shaped bend joining the two legs, each of the two legs having a terminal end.

3. The surgical assembly of claim 2, wherein the suture passes through a plurality of openings in the all-suture anchor along a length of the flexible body between the terminal ends of the two legs.

4. The surgical assembly of claim 3, wherein the suture only extends a single time through each of the plurality of openings.

5. The surgical assembly of claim 2, wherein the suture extends longitudinally down one leg of the flexible body and longitudinally up the other leg of the flexible body in a single direction without intersecting itself.

6. The surgical assembly of claim 1, wherein the all-suture anchor comprises monofilament, tape, braid, or mesh.

7. The surgical assembly of claim 1, wherein the suture comprises two end regions and an entirety of the suture, including the end regions, is slidable with respect to an entire longitudinal extent of the all-suture anchor in either direction.

8. The surgical assembly of claim 1, further comprising a cannula configured to allow passage of the forked distal end therethrough.

9. The surgical assembly of claim 8, wherein a distal portion of the cannula comprises a serrated edge for facilitating maintenance of the cannula on bone.

10. The surgical assembly of claim 9, wherein a distal portion of the cannula is angled relative to a longitudinal axis of the cannula, and at least a portion of the elongate member is flexible to permit the elongate member to conform to a shape of the cannula.

11. A surgical assembly comprising:
an all-suture anchor;
a suture slidably received by the all-suture anchor such that the all-suture anchor can bunch up relative to the suture;
an elongate member including a forked distal end; and
a proximal portion proximal to the elongate member, the proximal portion defining a circular groove;
wherein the all-suture anchor and the suture are received on the forked distal end such that the suture extends proximally along an external surface of the elongate member and through the proximal portion, and extends perpendicular to the elongate member across a diameter of the surgical assembly to the circular groove.

12. The surgical assembly of claim 11, wherein the all-suture anchor comprises a flexible body formed by two legs and a U-shaped bend joining the two legs, each of the two legs having a terminal end.

13. The surgical assembly of claim 12, wherein the suture passes through a plurality of openings in the all-suture anchor along a length of the flexible body between the terminal ends of the two legs.

14. The surgical assembly of claim 13, wherein the suture only extends a single time through each of the plurality of openings.

15. The surgical assembly of claim 12, wherein the suture extends longitudinally down one leg of the flexible body and longitudinally up the other leg of the flexible body in a single direction without intersecting itself.

16. The surgical assembly of claim 11, wherein the suture comprises two end regions and an entirety of the suture, including the end regions, is slidable with respect to an entire longitudinal extent of the all-suture anchor in either direction.

17. The surgical assembly of claim 11, further comprising a cannula configured to allow passage of the forked distal end therethrough.

18. The surgical assembly of claim 17, wherein a distal portion of the cannula comprises a serrated edge for facilitating maintenance of the cannula on bone.

19. The surgical assembly of claim 17, wherein a distal portion of the cannula is angled relative to a longitudinal axis of the cannula, and at least a portion of the elongate member is flexible to permit the elongate member to conform to a shape of the cannula.

* * * * *